(12) United States Patent
Bouhnik et al.

(10) Patent No.: US 11,285,663 B2
(45) Date of Patent: Mar. 29, 2022

(54) METHODS AND SYSTEMS FOR ADDITIVE MANUFACTURING OF COLLIMATORS FOR MEDICAL IMAGING

(71) Applicant: GE Precision Healthcare LLC, Milwaukee, WI (US)

(72) Inventors: Jean-Paul Bouhnik, Zichron Yaakov (IL); Moshe Levy, Zichron Yaakov (IL); Roee Khen, Haifa (IL); Nathan Hermony, Caesarea (IL); Yaron Hefetz, Herzeliya (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 117 days.

(21) Appl. No.: 16/820,345

(22) Filed: Mar. 16, 2020

(65) Prior Publication Data

US 2021/0283832 A1    Sep. 16, 2021

(51) Int. Cl.
| | | |
|---|---|---|
| *B29C 64/153* | (2017.01) |
| *B22F 3/10* | (2006.01) |
| *G01R 33/48* | (2006.01) |
| *A61B 6/06* | (2006.01) |
| *G21K 1/02* | (2006.01) |
| *G21K 1/10* | (2006.01) |
| *B33Y 80/00* | (2015.01) |
| *B33Y 10/00* | (2015.01) |

(52) U.S. Cl.
CPC .............. *B29C 64/153* (2017.08); *A61B 6/06* (2013.01); *B22F 3/10* (2013.01); *G01R 33/48* (2013.01); *G21K 1/02* (2013.01); *G21K 1/10* (2013.01); *B33Y 10/00* (2014.12); *B33Y 80/00* (2014.12)

(58) Field of Classification Search
CPC ......... A61B 6/4266; A61B 6/06; A61B 6/547; A61B 6/544; A61B 6/588; A61B 6/4291; A61B 6/4275; G01T 1/243
See application file for complete search history.

(56) References Cited

U.S. PATENT DOCUMENTS

| | | | |
|---|---|---|---|
| 9,064,611 B2 | 6/2015 | Freund et al. |
| 9,206,309 B2 | 12/2015 | Appleby et al. |
| 9,966,158 B2 | 5/2018 | Reitz et al. |
| 10,408,947 B2 | 9/2019 | Beacham et al. |
| 2005/0281701 A1 | 12/2005 | Lynch et al. |
| 2012/0085942 A1 | 4/2012 | Birman et al. |
| 2015/0094571 A1 | 4/2015 | Bouhnik et al. |
| 2015/0094574 A1 | 4/2015 | Bouhnik et al. |
| 2019/0223816 A1 | 7/2019 | Bouhnik et al. |
| 2019/0290224 A1 | 9/2019 | Clark et al. |
| 2021/0283832 A1* | 9/2021 | Bouhnik .................. A61B 6/06 |

FOREIGN PATENT DOCUMENTS

| | | | |
|---|---|---|---|
| DE | 102014217569 A1 | 3/2016 |
| DE | 102015225994 A1 | 6/2017 |
| WO | 2019149612 A1 | 8/2019 |

* cited by examiner

*Primary Examiner* — Don K Wong
(74) *Attorney, Agent, or Firm* — McCoy Russell LLP

(57) ABSTRACT

Methods and systems are provided for additive manufacturing of collimators for medical imaging applications. In one example, a collimator may include a plurality of collimator segments including a plurality of septa, wherein at least one collimator segment may be interlocked with at least one adjacent collimator segment via mating of one or more projections with one or more complementary recesses, each of the one or more projections including a lengthwise portion of at least one septum of the plurality of septa.

20 Claims, 11 Drawing Sheets

METHODS AND SYSTEMS FOR ADDITIVE MANUFACTURING OF COLLIMATORS FOR MEDICAL IMAGING

FIELD

Embodiments of the subject matter disclosed herein relate to medical imaging systems, and more particularly to additive manufacturing of collimators for nuclear medicine imaging systems.

BACKGROUND

Nuclear medicine (NM) imaging systems may include one or more detectors or detector heads for imaging a subject, such as a patient. For example, the detectors may be positioned adjacent to the subject on a gantry to acquire NM imaging data (e.g., radioactivity) with a wide field of view. Each detector may further be associated with a collimator which narrows and focuses acquired radiation for the detector. The acquired NM imaging data may then be used to generate a three-dimensional (3D) image of the subject. Accordingly, components may be machined to high precision such that correspondingly high imaging fidelity may be obtained. For example, additive manufacturing techniques (e.g., 3D printing) may be employed in order to achieve high reproducibility. However, fabrication of components for wide field of view applications may employ large manufacturing equipment and lengthy manufacturing times.

BRIEF DESCRIPTION

In one embodiment, a collimator may include a plurality of collimator segments including a plurality of septa, wherein at least one collimator segment may be interlocked with at least one adjacent collimator segment via mating of one or more projections with one or more complementary recesses, each of the one or more projections including a lengthwise portion of at least one septum of the plurality of septa.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
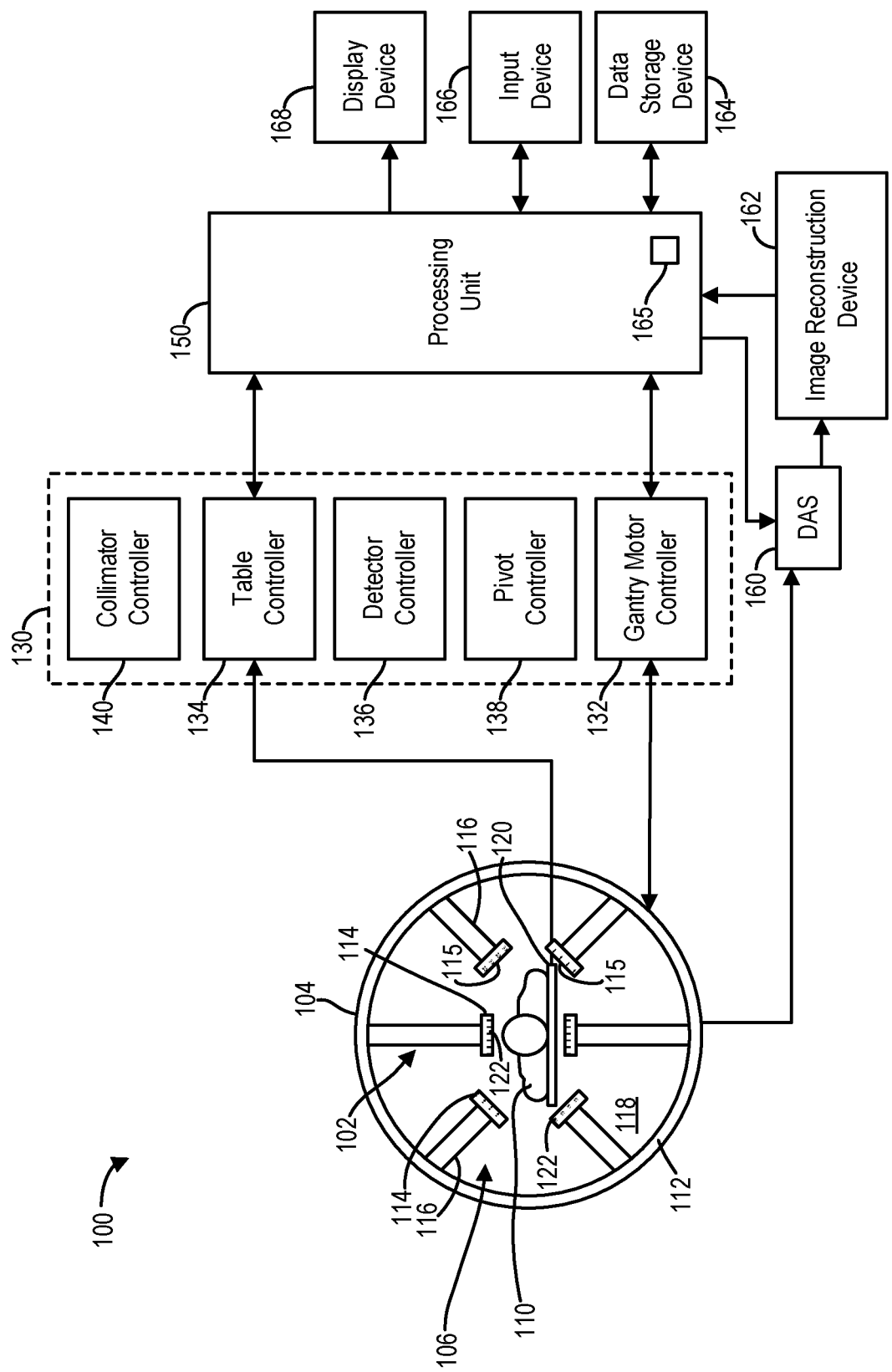
FIG. 1 shows a schematic block diagram of a nuclear medicine (NM) imaging system, according to an embodiment.

The following description relates to various embodiments of nuclear medicine (NM) imaging systems, and manufacturing collimators therefor. One example NM imaging system employing an exemplary detector array is depicted in FIG. 1. The detector array may include one or more imaging detectors, each of the one or more imaging detectors including a respective detector unit having a plurality of cadmium zinc telluride (CZT) modules registered to a collimator, such as the detector unit depicted in FIG. 10. Specifically, and as shown in FIG. 3, the collimator may be assembled from multiple collimator segments, wherein the collimator segments may be formed via additive manufacturing techniques, such as via the method of FIG. 2. Accordingly, numerous configurations of assembled collimators may be contemplated, such as the exemplary configurations shown in FIGS. 4A and 4B. In the assembled collimators, the collimator segments may be joined to one another with an adhesive. Further, each individual collimator segment may be manufactured so as to interlock with one or more further collimator segments, as shown in FIGS. 5-6B.

Figure 8:
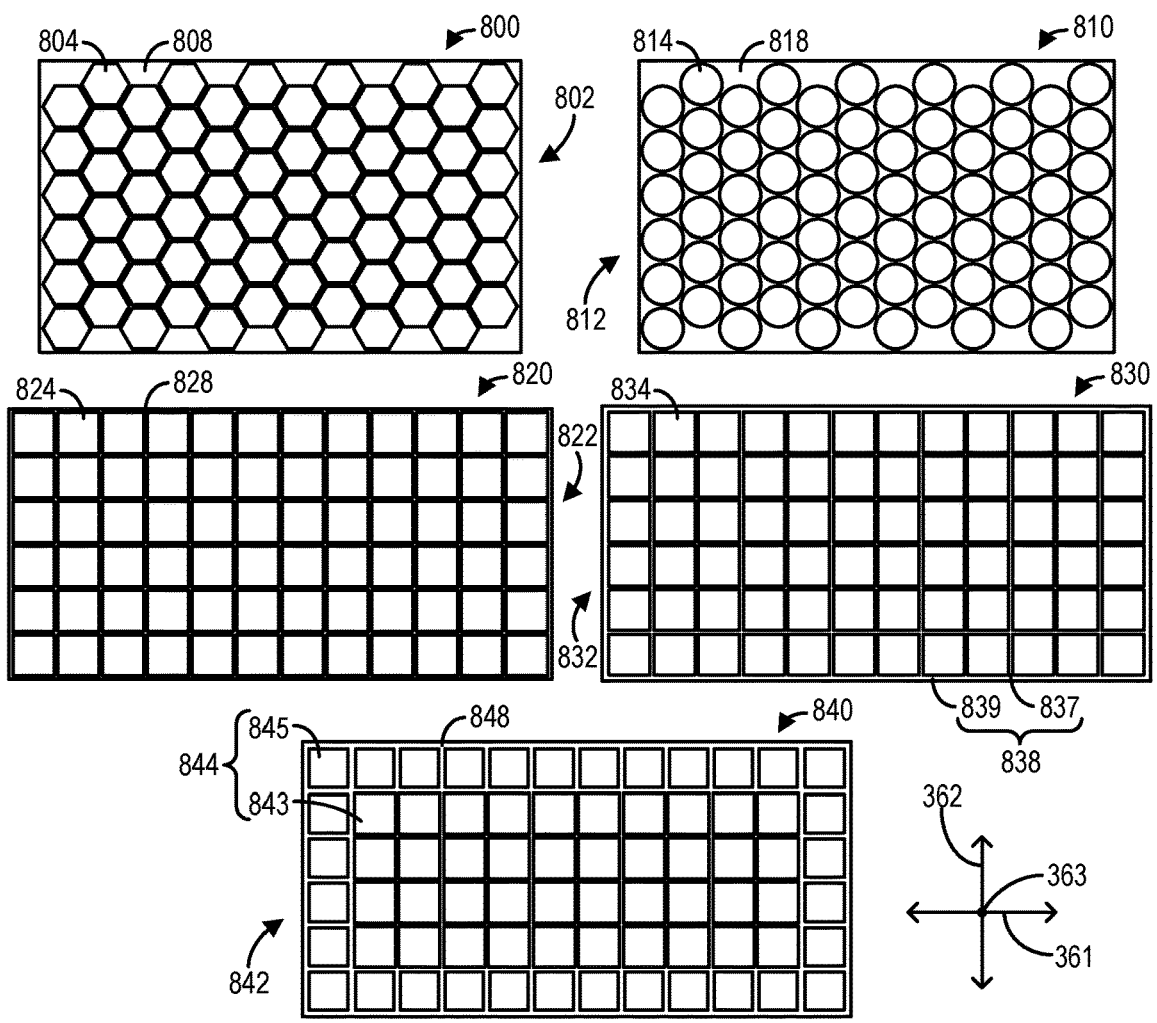
FIG. 8 shows schematic diagrams illustrating various exemplary collimator segment configurations having respective exemplary bore patterns.
Figure 9:
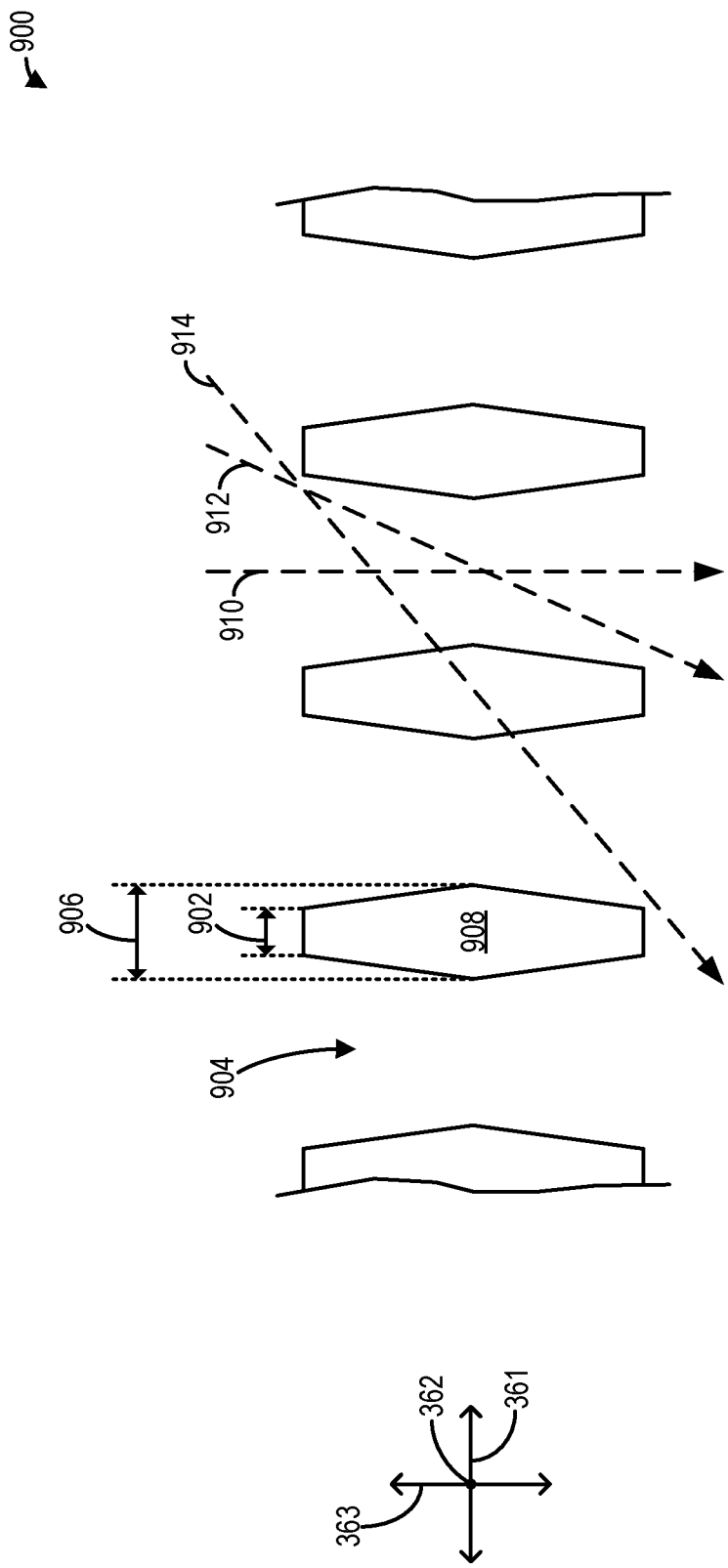
FIG. 9 shows a schematic diagram illustrating geometric considerations of radiation penetrating the collimator, according to an embodiment.

A given collimator segment may be characterized by at least a bore width, a bore pattern, and a septal thickness. Accordingly, two exemplary bore widths are compared in FIG. 7 and various exemplary collimator segment configurations having respective exemplary bore patterns are shown in FIG. 8. Further, variations of the septal thickness within the given collimator segment may decrease septal penetration, as illustrated in FIG. 9.

FIG. 1 is a schematic illustration of a NM imaging system 100 having a plurality of imaging detectors mounted on a gantry. The imaging detectors may be configured to rotate around a fixed pivot. The movement of the imaging detectors may be controlled to reduce the likelihood of, or avoid, collision among the moving imaging detectors and/or reduce the likelihood of one imaging detector obstructing the field of view of another imaging detector. For example, the NM imaging system in some embodiments provides coordinated swinging or pivoting motion of a plurality of imaging detectors or detector units therein.

In particular, a plurality of imaging detectors 102 are mounted to a gantry 104 and/or a patient support structure (not shown) (e.g., under a patient table 120), which may define a table support for the patient table 120. In the illustrated embodiment, the imaging detectors 102 are configured as a detector array 106 positioned around the subject 110 (e.g., a patient), as viewed in FIG. 1. The detector array 106 may be coupled directly to the gantry 104, or may be coupled via support members 112 thereto, to allow movement of the entire detector array 106 relative to the gantry 104 (e.g., rotational movement in the clockwise or counterclockwise direction as viewed in FIG. 1). Additionally, each of the imaging detectors 102 may include a detector unit 114, each of which may be mounted to a movable detector carrier 116 (e.g., a support arm or actuator that may be driven by a motor to cause movement thereof) that extends from the gantry 104. In some embodiments, each of the detector units 114 may be positioned outside of (e.g., at an end of) a respective detector carrier 116 nearest a center of an aperture 118 of the gantry 104. In additional or alternative embodiments not shown at FIG. 1, at least some of the detector units 114 may be positioned within (e.g., within an end of) a respective detector carrier 116 nearest the center of the aperture 118 of the gantry 104.

In some embodiments, the detector carriers 116 may allow movement of the detector units 114 toward and away from the subject 110, such as linearly. Thus, in the illustrated embodiment, the detector array 106 is around the subject 110 and may allow linear movement of the detector units 114, such as toward or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112 and/or gantry 104, which in various embodiments allows the detector units 114 to move linearly toward and away from the support member 112, such as radially inward and outwards for positioning adjacent the subject 110. For example, as described herein, the detector units 114 may be controlled to move independently of each other toward or away from the subject 110, as well as capable of rotational, pivoting, or tilting movement in some embodiments.

Each of the imaging detectors 102 may include one or more detector units 114 coupled to respective detector carrier(s) 116 and may be formed of a plurality of CZT tiles or modules. As an example, each of the detector units 114 may be 40×52 cm in size and may be composed of 130 CZT pixelated modules (not shown at FIG. 1), such that a wide field of view may be imaged. As such, each module may be 4×4 cm in size. Further, each module may have 16×16 (=256) pixels, such that each pixel may be 2.5×2.5 mm in size. In some embodiments, each detector unit 114 may include a plurality of modules, such as an array of 10×13 modules, 8×13 modules, 7×13 modules, etc. However, different configurations and array sizes may be contemplated without departing from the scope of the present disclosure.

It should be understood that the imaging detectors 102 and/or the detector units 114 may be different sizes and/or shapes with respect to each other, such as square, rectangular, circular, or another shape. An actual field of view of each of the imaging detectors 102 may be directly proportional to the size and shape of the respective imaging detector 102 and detector unit 114. In some embodiments, each of the imaging detectors 102 may have a same configuration as each other imaging detector 102. Thus, in such embodiments, each of the detector units 114 respectively included in the imaging detectors 102 may have a same configuration as each other detector unit 114. In one embodiment, each of the detector units 114 may have a rectangular shape, and each CZT module in a given row of CZT modules may be equidistant from a surface 115 of a given detector unit 114.

It will be appreciated that a number of imaging detectors 102 may vary between embodiments and may be limited by practical constraints and not by the exemplary embodiments discussed in the present disclosure. A lower limit of the number of imaging detectors 102 may be selected to provide a threshold amount of imaging coverage based on the field of view of a given imaging detector 102. An upper limit of the number of imaging detectors may be selected to prevent any given imaging detector 102 obscuring the field of view of another imaging detector 102. In exemplary embodiments, 1, 2, 3, 4, 5, 6, 7, 8, 9, 10, 11, or 12 imaging detector(s) 102 may be included in the detector array 106.

The gantry 104 may be formed with the aperture 118 (e.g., cylindrical opening or bore) therethrough as illustrated. The patient table 120 may be configured with a support mechanism, such as the patient support structure, to support and carry the subject 110 in one or more of a plurality of viewing positions within the aperture 118 and relative to the imaging detectors 102. Alternatively, the gantry 104 may include a plurality of gantry segments (not shown), each of which may independently move a given support member 112 or one or more of the imaging detectors 102.

The gantry 104 may also be configured in other shapes, such as a "C," "H," or "L," for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc-shaped and the support members 112 movable along the arc to position the imaging detectors 102 at different locations along the gantry 104. In some embodiments, the imaging detectors 102 may also be independently movable along the gantry 104.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head-to-toe direction of the subject 110), image data specific for a larger FOV may be acquired more quickly.

The detector units 114 may be configured to acquire radiation emitted from the subject 110. As such, each of the detector units 114 may include a radiation detection face, which may be directed toward the subject 110 or a region of interest within the subject 110. The radiation detection faces may each be covered by or have coupled thereto a collimator 122. The actual field of view for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include slanthole, pinhole, parallel-beam converging, diverging fan-beam, converging or diverging cone-beam, multi-bore converging, multi-bore converging fan-beam, multi-bore converging cone-beam, multi-bore diverging, or other types of collimators.

The detector units 114 may be configured such that a given collimator 122 may be exchanged for another collimator, e.g., to suit a different imaging application. For example, a slanthole collimator may be used to direct radiation to and from an organ partially blocked from view.

As another example, a pinhole collimator may be used to image a relatively small structure, such as a thyroid or a joint. In some embodiments, a given detector unit 114 may be fit with one type of collimator 122 and another detector unit 114 may be fit with another type of collimator 122. In some embodiments, portions of the collimator 122 may be stacked in a layered configuration with respect to a given detector unit 114, such that a portion may be exchanged and another portion may remain fit to the given collimator 122. It will therefore be appreciated that many configurations of collimators 122 may be contemplated and implemented within the scope of the present disclosure. In this way, a breadth of imaging applications may be increased by varying types and configurations of collimators 122 in the detector units 114.

Multi-bore collimators may be constructed to be registered to pixels of the detector units 114, which in one embodiment are CZT detectors. However, other materials may be used. Registered collimation may improve spatial resolution by forcing photons going through one bore to be collected primarily by one pixel. In other embodiments, and as described in detail below with reference to FIG. 7, multiple bores (e.g., 4 bores in a 2×2 configuration) may be uniquely registered to one pixel. Additionally, registered collimation may improve a sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

In some embodiments, the collimator 122 may be a dual-pitch collimator, wherein a pitch of the collimator 122 may be twice a pitch of a corresponding detector unit 114 (that is, the collimator 122 may have a double pitch compared to the pitch of the corresponding detector unit 114). Implementing a dual-pitch collimator may reduce both a length of the collimator 122 (e.g., by half) and a diameter of the corresponding detector unit 114. Thus, for example, a smaller overall size of the detector unit 114 and the collimator 122 may be positioned closer to the subject 110 while avoiding collision with other imaging detectors 102 having other detector units 114.

It will be appreciated that the collimator 122 and the corresponding imaging detector 102 may have other relative pitches. In some embodiments, the pitch of the collimator 122 may be half the pitch of the corresponding imaging detector 102. In other embodiments, the pitch of the collimator 122 may be the same as the pitch of the corresponding imaging detector 102. In other embodiments, the pitch of the collimator 122 may be one and a half times the pitch of the corresponding imaging detector 102. In other embodiments, the pitch of the collimator 122 may be four times the pitch of the corresponding imaging detector 102.

In wide field of view applications, particularly large collimators 122 may be implemented to register with correspondingly large detector arrays. As such, opportunity for machining imprecision may also increase. In some embodiments, precision (and thereby imaging resolution and fidelity) may be retained by manufacturing smaller collimator segments via an additive manufacturing technique, such as three-dimensional (3D) printing. Such piecewise manufacturing may further improve a structural integrity of the assembled collimator and may increase an overall manufacturing speed by manufacturing collimator segments in parallel. Further, complex structures, such as variations in septal thickness and specific geometric configurations may be easily realized via additive manufacturing. Accordingly, a method for piecewise additive manufacturing of a collimator is discussed in detail below with reference to FIG. 2.

In some embodiments, the detector units 114 may move such that a surface thereof is as close as possible to the subject 110, thereby increasing an imaging sensitivity of the NM imaging system 100. As a result, however, a pivoting motion of the detector units 114 may be limited in such embodiments to avoid or limit contact with the subject 110.

A controller unit 130 may control the movement and positioning of the patient table 120, imaging detectors 102, gantry 104, and/or the collimators 122. A range of motion before or during an acquisition, or between different image acquisitions, is set to maintain the actual FOV of each of the imaging detectors 102 directed, for example, toward or "aimed at" a particular area or region of the subject 110 or along the entire subject 110.

The controller unit 130 may have a gantry motor controller 132, table controller 134, detector controller 136, pivot controller 138, and collimator controller 140. The controllers 132, 134, 136, 138, 140 (that is, the controller unit 130) may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry motor controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. As a specific example, a large region of interest of the subject 110 (e.g., metastasis) may be imaged with relatively few imaging detectors 102 by moving the patient table 120 through an area of the gantry 104 having the imaging detectors 102 such that the same imaging detectors 102 may perform a scan of the entire region of interest.

The detector controller 136 may control movement of each of the imaging detectors 102 to move closer to and farther from a surface of the subject 110, such as by controlling translating movement of the detector carriers 116 linearly toward or away from the subject 110 (e.g., sliding or telescoping movement). Optionally, the detector controller 136 may control movement of the detector carriers 116 to allow coordinated movement of the detector array 106. The pivot controller 138 may control pivoting, rotating, or swinging movement of the detector units 114 at ends of the detector carriers 116, and/or the detector carrier 116. For example, one or more of the detector units 114 or detector carriers 116 may be pivoted or swung about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller"

may be used to indicate a collective name for all motion controllers (e.g., controllers 132, 136, 138). It should be noted that the various controllers may be combined, for example, the detector controller 136 and pivot controller 138 may be combined to provide the different movements described herein.

Prior to acquiring an image of the subject 110 or a portion of the subject 110, the imaging detectors 102, gantry 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data. Positioning may be accomplished manually by the operator and/or automatically, which may include using other images acquired before the current acquisition, such as by another imaging modality such as computed tomography (CT), magnetic resonance imaging (MRI), x-ray, positron emission tomography (PET), or ultrasound. Additionally, the detector units 114 may be configured to acquire non-NM data, such as x-ray CT data.

After the imaging detectors 102, gantry 104, patient table 120, and/or collimators 122 are positioned, one or more images may be acquired by one or more of the imaging detectors 102 being used, which may include pivoting or swinging motion of one or more of the detector units 114, which may pivot, rotate, or swing to different degrees or between different ranges of angles. The image data acquired by each imaging detector 102 may be combined and reconstructed into a composite image, which may include two-dimensional (2D) images, a three-dimensional (3D) volume, or a 3D volume over time, e.g., four dimensions (4D).

In one embodiment, the imaging detectors 102, gantry 104, patient table 120, and/or collimators 122 may remain stationary after being initially positioned. In another embodiment, an effective field of view for one or more of the imaging detectors 102 may be increased by movement such as pivoting, rotating, or swinging one or more of the imaging detectors 102, rotating the detector array 106 with the gantry 104, adjusting one or more of the collimators 122, or moving the patient table 120.

In various embodiments, a data acquisition system (DAS) 160 may receive electrical signal data produced by the imaging detectors 102 and converts the electrical signal data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the NM imaging system 100, or may be located remotely. Additionally, a user input device 166 may be provided to receive user inputs (e.g., control commands), as well as a display 168 for displaying images.

Additionally, a detector position controller 165 may also be provided, which may be implemented in hardware, software, or a combination thereof. For example, as shown in FIG. 1, the detector position controller 165 may form part of, or operate in connection with, the processing unit 150. In some embodiments, the detector position controller 165 may be a module that operates to control the movement of the imaging detectors 102, including the detector units 114, such that coordinated or synchronized movement is provided as described herein. It should be noted that movement of a plurality of the imaging detectors 102 and/or detector units 114 may be performed at the same time (e.g., simultaneously or concurrently) or at different times (e.g., sequentially or step-wise, such as back and forth between two detector units 114). It also should be understood that when referring to a detector unit, such a detector unit may include one or multiple detector modules (e.g., CZT modules).

Figure 2:
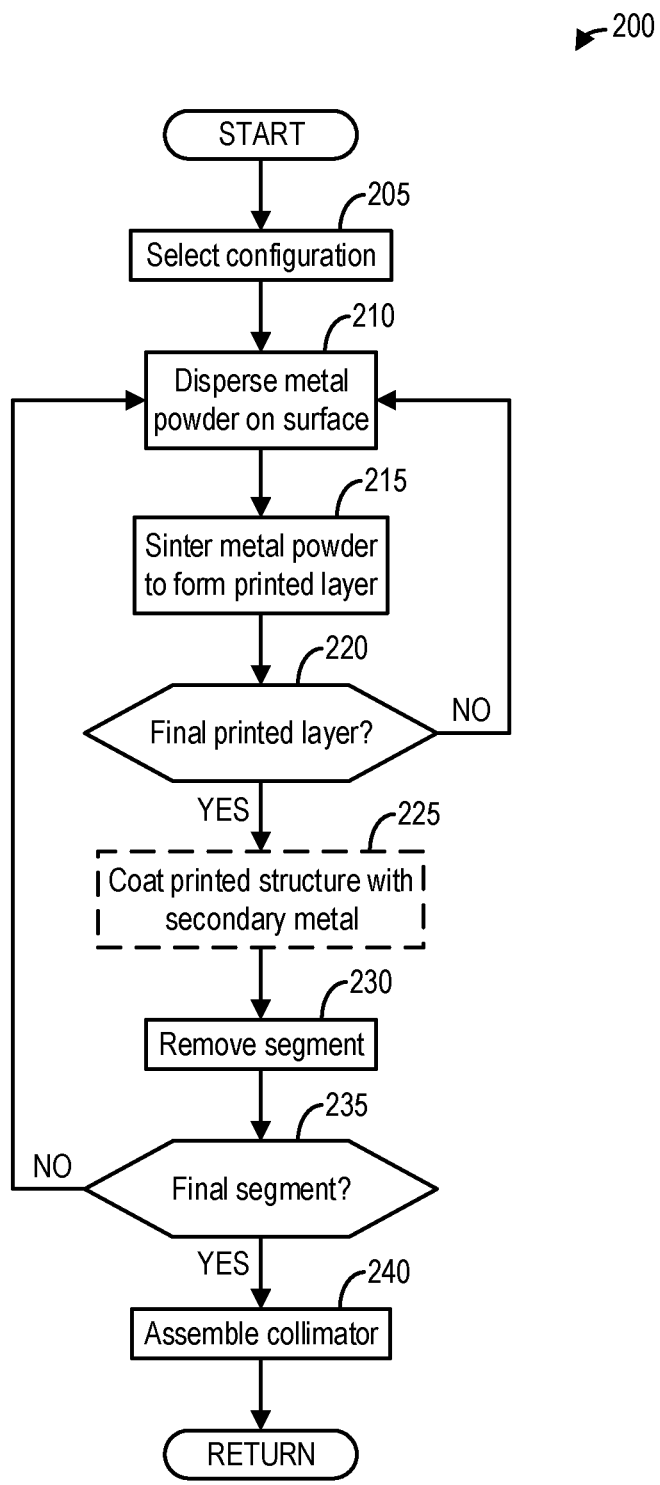
FIG. 2 shows a flow chart of a method for assembling a collimator with additive manufacturing techniques, according to an embodiment.
Figure 3:
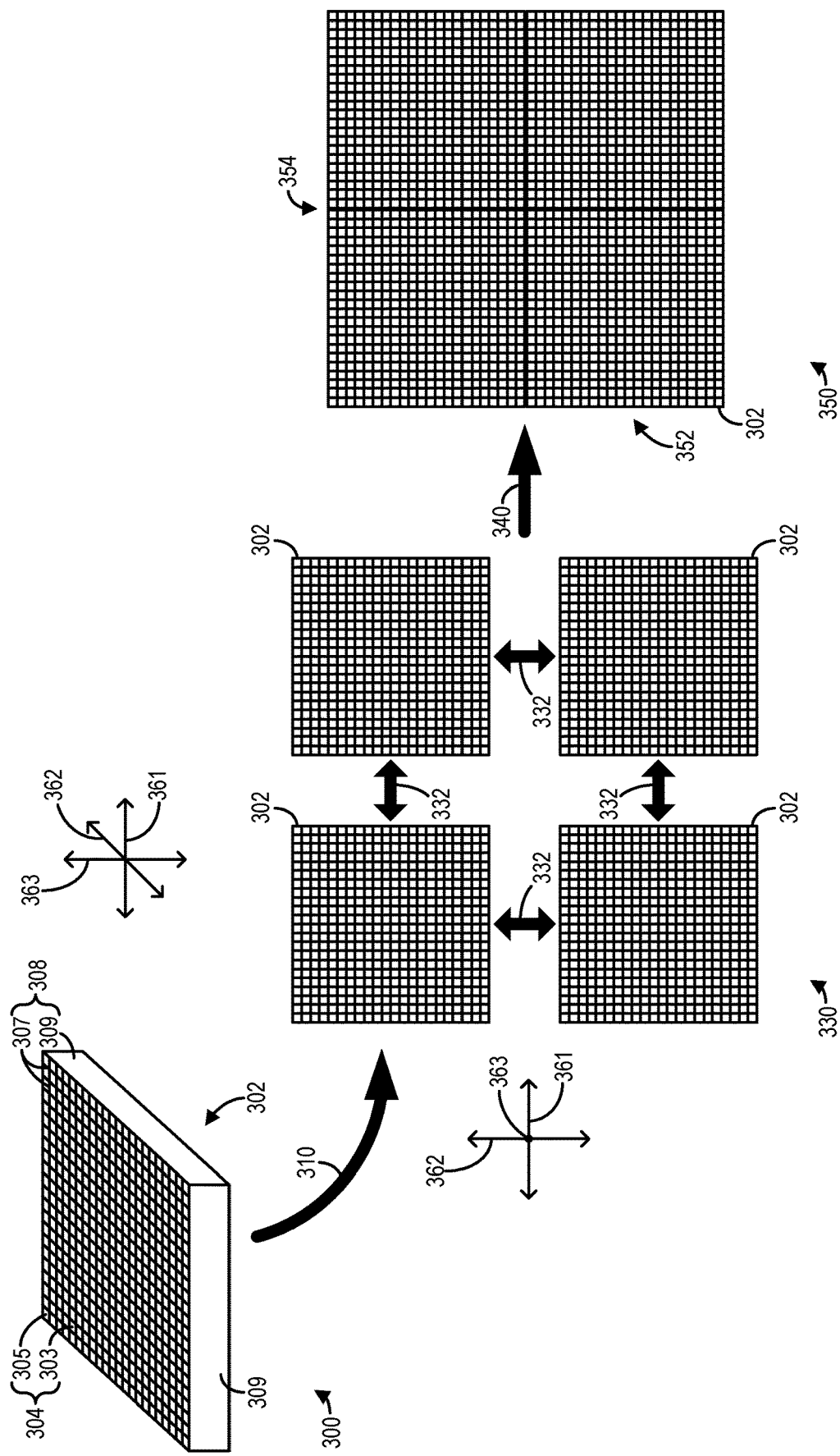
FIG. 3 shows schematic diagrams illustrating a first exemplary assembly process of the collimator from multiple collimator segments, according to an embodiment.

Referring now to FIG. 2, a flow chart is depicted, showing a method 200 for piecewise assembly of a collimator via additive manufacturing of individual collimator segments. Though method 200 is described below with regard to the systems and components depicted in FIG. 1, it should be appreciated that method 200 may be implemented with regard to other systems and components without departing from the scope of the present disclosure. For example, in some embodiments, method 200 may be implemented to assemble the collimator 122 for use in the NM imaging system 100.

Method 200 may begin at 205, where a collimator assembly configuration may be selected. As detailed below with reference to FIGS. 4A and 4B, various geometric patterns of collimator segments may be contemplated by those of at least ordinary skill in the art. Accordingly, selecting the collimator assembly configuration may at least depend upon a size of the collimator (e.g., 122), a number of CZT modules to which the collimator may be registered, a number of modules within the detector units, an available machining precision of the additive manufacturing equipment, and a desired structural integrity of the collimator.

In some embodiments, selecting the collimator assembly configuration may further depend upon a size of the additive manufacturing equipment. As discussed in detail below with reference to FIGS. 4A and 4B, a manufacturing area of the additive manufacturing equipment may limit an overall size of an individual collimator segment to be relatively small. Such small collimator segments, when paired with correspondingly large interfacial perimeters, may provide a high overall interfacial surface area in the assembled collimator such that many collimator segments may be joined (e.g., via an adhesive) at a multitude of surfaces. As such, the collimator assembly configuration may be selected such that the collimator segments have a high average perimeter to average size ratio.

Further, a configuration of each individual collimator segment may be selected so as to interface with other collimator segments with high structural integrity. For example, and as discussed below with reference to FIG. 8, bore widths and septal thicknesses may be varied within a given collimator segment. Such variations in bore width and septal thickness may also reduce undesired septal penetration of acquired radiation. For example, and as discussed below with reference to FIG. 9, the septal thickness may increase along a length of the bores towards an interior of the collimator. As such, radiation may be acquired by CZT modules registered to the assembled collimator (e.g., 122) with increased fidelity.

Collimators are typically formed from high-Z metals so as to increase radiation shielding (that is, reduce septal penetration). Accordingly, direct metal laser sintering may be utilized such that single-metal or mixed-metal structures may be 3D printed. Individual layers of metal powder may be dispersed onto a substrate and sintered thereon such that a given structure may be additively manufactured by progressive accumulation of the sintered, or printed, layers. Additive manufacturing of collimators via direct metal laser sintering may increase a machining precision through fine control of both metal powder dispersion (e.g., 210) and the subsequent laser sintering (e.g., 215) as implemented on machine-readable instructions stored in memory and executable by a processor of a given 3D printer.

Accordingly, at 210, method 200 may include dispersing a metal powder on a surface of a substrate. The substrate may be a base plate of the additive manufacturing equipment, a base plate of a component to be manufactured, or a metal structure already having multiple metal layers sintered thereon (e.g., a partially manufactured component). In some embodiments, the metal powder may be a tungsten powder. It will be appreciated that other high-Z metals may be selected as the metal powder, such as lead, thallium, tantalum, bismuth, osmium, platinum, gold, rhenium, etc.

As tungsten has the highest melting point of any metal, high temperatures may be desired for sintering if tungsten powder is selected. However, the laser may not have sufficient time or power to completely melt the tungsten powder. As such, voids and cracks may be generated in the resulting sintered layer, which may decrease a structural integrity of the assembled collimator, as well as radiation shielding properties due to such decreased metal density (e.g., air in the formed voids and cracks may have substantially no attenuation for blocking radiation leaks).

To reduce such voids and cracks, a coated tungsten powder may instead be provided. The coated tungsten powder may include a substantially tungsten core continuously or discretely coated with a filler metal selected to have a high Z value (e.g., for increasing radiation shielding), high density (e.g., for increasing both radiation shielding and structural integrity), and low melting point (e.g., for increasing sintering efficacy). In other embodiments, the tungsten powder may be uncoated, and may be dispersed on the substrate along with an additional powder composed of the filler metal. In some embodiments, the filler metal may include a transition metal, a main group metal or metalloid. For example, the filler metal may include one or more of lead, thallium, molybdenum, tantalum, bismuth, copper, iron, and antimony. In some embodiments, the filler metal may be provided in each layer as 1%, 2%, 5%, 10%, 15%, or 20% of a total metal content. Additionally or alternatively, a vacuum or low-pressure environment may be used to decrease void and crack formation.

At 215, method 200 may include sintering the metal powder to form a printed layer. The laser may sinter the metal powder in a predetermined pattern and may thereby incrementally manufacture the collimator via sintering of successive layers. At 220, method 200 may include determining if the formed printed layer is the final printed layer for a given metal structure (e.g., collimator segment). If the printed layer is not the final printed layer, then method 200 may include returning to 210 to disperse metal powder and then, at 215, sinter the metal powder to form another printed layer thereon.

If the printed layer is the final printed layer, then method 200 may optionally proceed to 225 to coat the printed structure with a secondary metal (in addition to the tungsten and/or filler metal powders). In some embodiments, the secondary metal may first be heated to a molten state, and the printed structure may then be dipped into the molten secondary metal such that the molten secondary metal may coat outer surfaces of the printed structure and may seep into voids and cracks thereof. Before solidifying, the molten secondary metal may be blown out of collimator bores formed in the printed structure, such that radiation may effectively pass through the finally-assembled collimator to registered CZT modules. In additional or alternative embodiments, the predetermined pattern of the printed layers may have a smaller volume (e.g., thinner septa) than in the assembled collimator, as the coating of the secondary metal may provide any desired remaining volume upon solidification thereof.

As such, the collimator segment may be formed. At 230, method 200 may include removing the collimator segment from the additive manufacturing equipment. At 235, method 200 may include determining if the formed collimator segment is the final collimator segment to be formed for a given collimator assembly configuration. If the formed collimator segment is not the final collimator segment, method 200 may include returning to 210 to disperse metal powder and begin forming another collimator segment.

If the formed collimator segment is the final collimator segment, method 200 may include proceeding to 240 to assemble the collimator (e.g., 122) according to the selected collimator assembly configuration. Specifically, the formed collimator segments may be aligned with and joined to one another at peripheral interfaces (as discussed in detail below with reference to FIG. 3). For example, pairs of the formed collimator segments may be interlocked by overlapping lengthwise portions of septa in each pair of formed collimator segments. It will be appreciated that uniformity provided by the additive manufacturing techniques disclosed herein may help maintain distances between pairs of collimator segments.

In some embodiments, at least some of the formed collimator segments may be joined via application of an adhesive (e.g., a glue, cement, mucilage, paste, etc.). In additional or alternative embodiments, at least some of the formed collimator segments may be joined to one another via pairwise interlocking of the collimator segments (as discussed in detail below with reference to FIGS. 5-6B). In one embodiment, each of the formed collimator segments may be interlocked with one or more other formed collimator segments such that every formed collimator segment is interlocked with another formed collimator segment to assemble the collimator. Method 200 may then end.

Referring now to FIG. 3, schematic diagrams 300, 330, and 350 illustrating a first exemplary assembly process of a collimator 352 from multiple collimator segments 302 are depicted according to one embodiment. In one embodiment, the assembled collimator 352 may be the collimator 122 as implemented in the NM imaging system 100. It will be appreciated that in FIG. 3, and in FIGS. 4A-10 (described in more detail below), mutually perpendicular axes 361, 362, and 363 may define a three-dimensional space relative to schematic diagrams 300, 330, and 350. Accordingly, schematic diagram 300 depicts a projected view in the three-dimensional space and schematic diagrams 330 and 350 depict top views in a plane defined by the axes 361 and 362, where the axis 363 is normal to the plane of the top views.

Schematic diagram 300 depicts one collimator segment 302. As shown, the collimator segment 302 may be configured as a rectangular prism. However, it will be appreciated that other configurations (e.g., hexagonal prisms, triangular prisms) may be contemplated by those of at least ordinary skill in the art. As a further example, the collimator segment 302 may be configured as multiple, aggregated rectangular prisms, where each rectangular prism may be configured so as to be uniquely registered to a CZT module of a detector unit (e.g., 114).

The collimator segment 302 may have a plurality of bores 304, arranged in a repeating pattern. As shown, the plurality of bores 304 may be configured in a grid, where pairs of adjacent bores 304 are separated by one of a plurality of septa 308 therebetween. The plurality of bores 304 may include a plurality of central bores 303 and a plurality of peripheral bores 305, and the plurality of septa 308 may include a plurality of central septa 307 and a plurality of interfacial septa 309. The plurality of central bores 303 may be defined as those bores 304 which are not adjacent to any interfacial septum 309, and the plurality of peripheral bores 305 may be defined as those bores 304 which are adjacent to any interfacial septum 309. Further, the plurality of interfacial septa 309 may be defined as those septa 308 which circumscribe the collimator segment 302 in a plane defined by the axes 361 and 362, and the plurality of central septa 307 may be defined as those septa 308 which intersect the collimator segment 302 in the plane defined by the axes 361 and 362. For example, the collimator segment 302 depicted by schematic diagram 300 may include four interfacial septa 309, where two interfacial septa 309 are visible in the projected view and two interfacial septa 309 are obscured in the projected view.

As represented by directional arrow 310, multiple collimator segments 302 may be aligned with one another according to a collimator assembly configuration. Accordingly, schematic diagram 330 depicts four collimator segments 302 aligned according to a square collimator assembly configuration. However, it will be appreciated that other collimator assembly configurations may be contemplated by those of at least ordinary skill in the art, such as the various exemplary collimator assembly configurations as discussed below with reference to FIGS. 4A and 4B.

As represented by bidirectional arrows 332, the collimator segments 302 may be joined together in a pairwise manner. In the first exemplary assembly process depicted in FIG. 3, the collimator segments 302 may include substantially flat interfacial septa 309. As such, and as represented by directional arrow 340, pairs of adjacent collimator segments 302 may be brought into face-sharing contact with one another according to the collimator assembly configuration, such that a first interfacial septum 309 of a first collimator segment 302 in a given pair of collimator segments 302 may be in face-sharing contact with a second interfacial septum 309 of a second collimator segment 302 in the given pair of collimator segments 302. Accordingly, and as shown in schematic diagram 350, interfaces 354 may be formed between the pairs of adjacent collimator segments 302 where the interfacial septa 309 come into face-sharing contact with one another. Once each collimator segment 302 is joined together according to the collimator assembly configuration, the collimator 352 may be assembled. In some embodiments, an adhesive (e.g., a glue, cement, mucilage, paste, etc.) or adhesive layer may be included between surfaces of the interfacial septa 309 forming the interfaces 354 such that the collimator segments 302 may be joined together according to the collimator assembly configuration. In additional or alternative embodiments, the adhesive or the adhesive layer may be restricted in the collimator 352 to the surfaces of the interfacial septa 309 forming the interfaces 354. That is, each of the collimator segments 302 may be manufactured as a single, monolithic piece without the adhesive, and then, following manufacturing, the collimator segments 302 may be joined to one another via the adhesive.

Figure 4A:
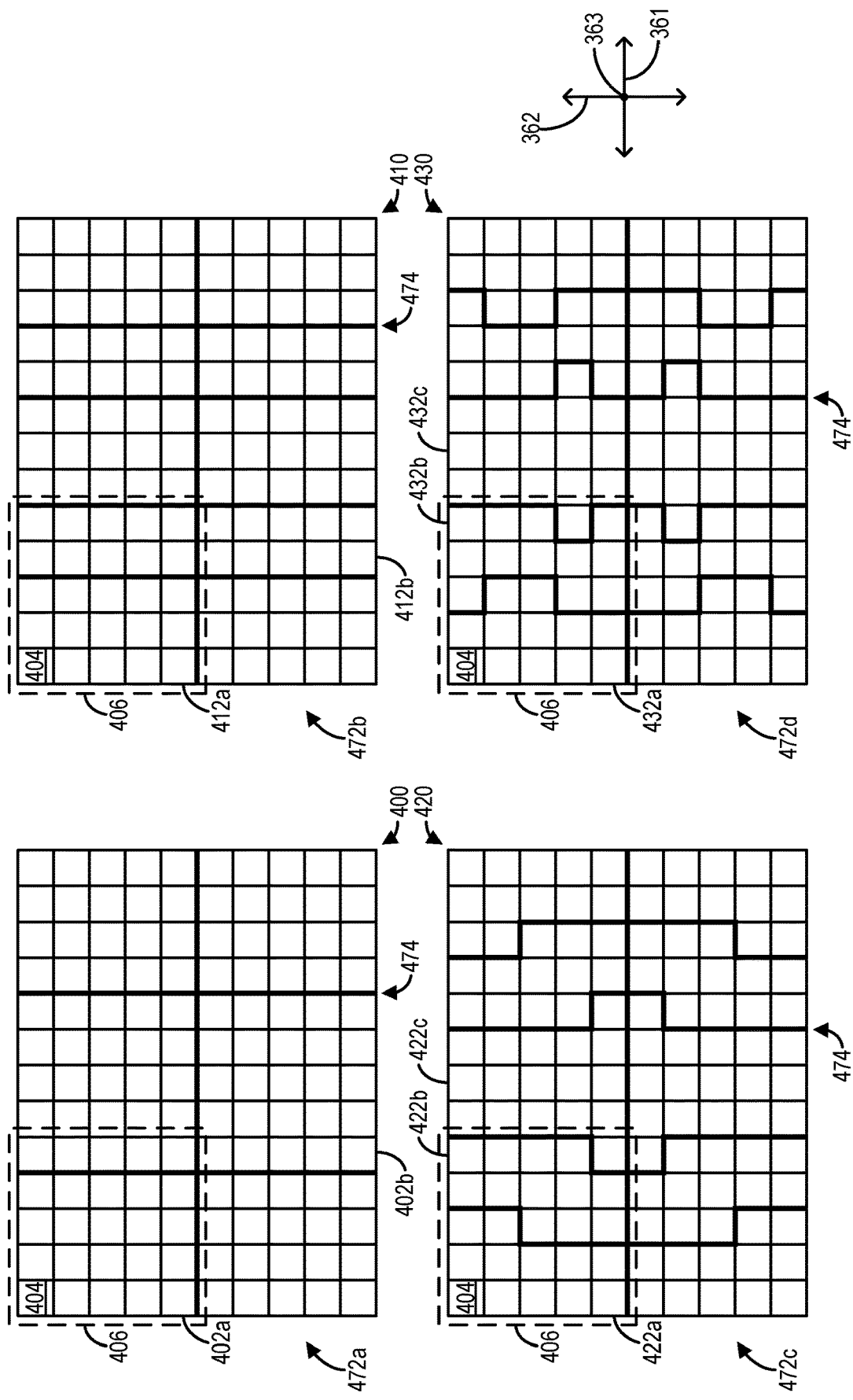
FIGS. 4A and 4B show schematic diagrams illustrating various exemplary assembled collimators, according to an embodiment.
Figure 4B:
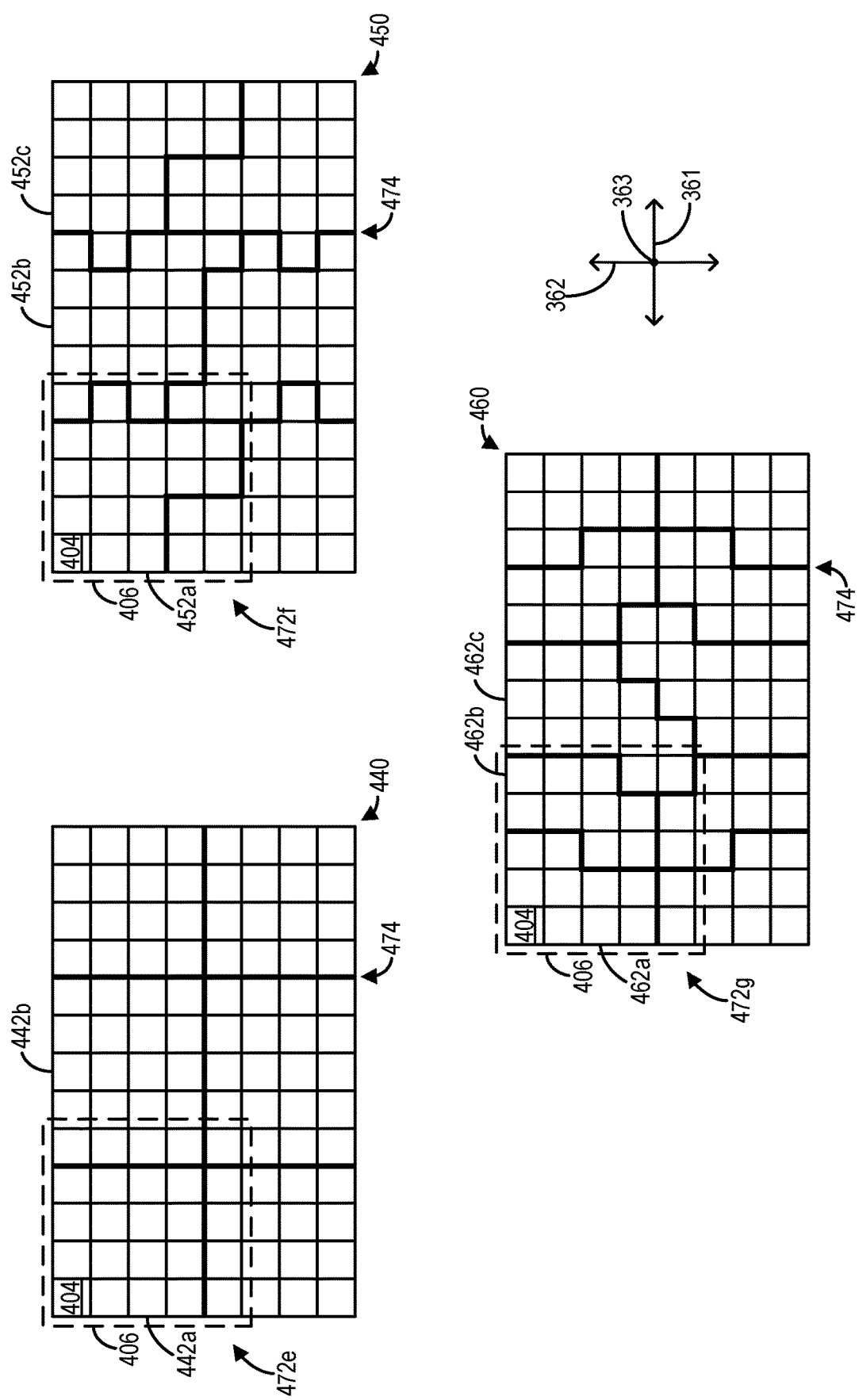
Figure 5:
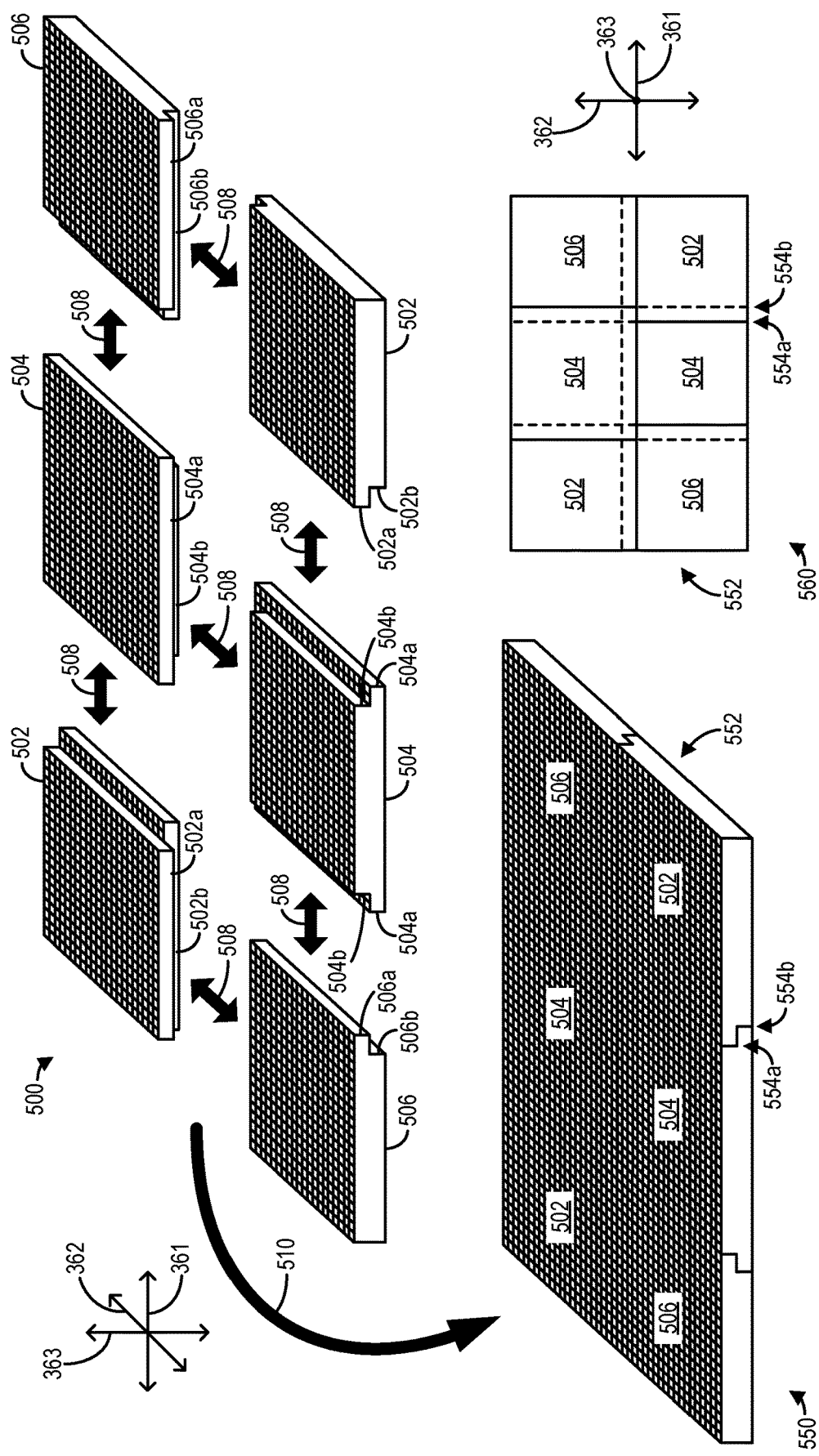
FIG. 5 shows schematic diagrams illustrating a second exemplary assembly process of the collimator from multiple collimator segments, according to an embodiment.

Referring now to FIGS. 4A and 4B, schematic diagrams 400, 410, 420, 430, 440, 450, and 460 respectively illustrating exemplary collimator assembly configurations of collimators 472a, 472b, 472c, 472d, 472e, 472f, and 472g are depicted. It will be appreciated that schematic diagrams 400, 410, 420, 430, 440, 450, and 460 may depict top views of the exemplary collimator assembly configurations similar to the top views of schematic diagrams 330 and 350, as shown in FIG. 3. Further, schematic diagrams 400, 410, 420, 430, 440, 450, and 460 may depict collimators implementable in a variety of systems, e.g., medical imaging systems. For example, in some embodiments, each of schematic diagrams 400, 410, 420, 430, 440, 450, and 460 may depict a collimator for use in an NM imaging system, such as the collimator 122 and the NM imaging system 100, as shown in FIG. 1.

The collimator assembly configurations are depicted in a simplified grid, wherein each cell 404 represents a portion of a given collimator segment uniquely registered to a CZT module of a detector unit (e.g., 114). It will be appreciated that each of the collimators 472a, 472b, 472c, 472d, 472e, 472f, and 472g may correspond to a rectangular array having any number of cells 404. For example, each of the collimators 472a, 472b, 472c, 472d, 472e, 472f, and 472g may have 7×13 cells 404, 8×13 cells 404, 10×13 cells 404, etc. which may respectively register to a detector array having 7×13 modules, 8×13 modules, 10—13 modules, etc. As shown, the exemplary collimator assembly configurations depicted in schematic diagrams 400, 410, 420, and 430 may include 10×13 cells 404, and the exemplary collimator assembly configurations depicted in schematic diagrams 440, 450, and 460 may include 8×13 cells 404.

In a first exemplary embodiment, and as shown by schematic diagram 400, the collimator 472a may be assembled from four collimator segments 402a and two collimator segments 402b according to a first exemplary collimator assembly configuration. Specifically, the four collimator segments 402a may each have 20 cells 404 arranged in an array of 5×4 cells 404, and the two collimator segments 402b may each have 25 cells 404 arranged in an array of 5×5 cells 404.

In a second exemplary embodiment, and as shown by schematic diagram 410, the collimator 472b may be assembled from six collimator segments 412a and four collimator segments 412b according to a second exemplary collimator assembly configuration. Specifically, the six collimator segments 412a may each have 15 cells 404 arranged in an array of 5×3 cells 404, and the four collimator segments 412b may each have 10 cells 404 arranged in an array of 5×2 cells 404.

In a third exemplary embodiment, and as shown by schematic diagram 420, the collimator 472c may be assembled from four collimator segments 422a, four collimator segments 422b, and two collimator segments 422c according to a third exemplary collimator assembly configuration. Specifically, the four collimator segments 422a may each have 12 cells 404 arranged in five rows parallel to the axis 361, where, in a sequential order along the axis 362, a first row may have three cells 404, a second row may have three cells 404, a third row may have two cells 404, a fourth row may have two cells 404, and a fifth row may have two cells 404. Further, the four collimator segments 422b may each have 12 cells 404 arranged in five rows parallel to the axis 361, where, in a sequential order along the axis 362, a first row may have two cells 404, a second row may have two cells 404, a third row may have three cells 404, a fourth row may have three cells 404, and a fifth row may have two cells 404. Further, the two collimator segments 422c may each have 17 cells 404 arranged in five rows parallel to the axis 361, where, in a sequential order along the axis 362, a first row may have three cells 404, a second row may have three cells 404, a third row may have three cells 404, a fourth row may have three cells 404, and a fifth row may have five cells 404.

In a fourth exemplary embodiment, and as shown by schematic diagram 430, the collimator 472*d* may be assembled from four collimator segments 432*a*, four collimator segments 432*b*, and two collimator segments 432*c* according to a fourth exemplary collimator assembly configuration. Specifically, the four collimator segments 432*a* may each have 12 cells 404 arranged in five rows parallel to the axis 361, where, in a sequential order along the axis 362, a first row may have two cells 404, a second row may have three cells 404, a third row may have three cells 404, a fourth row may have two cells 404, and a fifth row may have two cells 404. Further, the four collimator segments 432*b* may each have 12 cells 404 arranged in five rows parallel to the axis 361, where, in a sequential order along the axis 362, a first row may have three cells 404, a second row may have two cells 404, a third row may have two cells 404, a fourth row may have two cells 404, and a fifth row may have three cells 404. Further, the two collimator segments 432*c* may each have 17 cells 404 arranged in five rows parallel to the axis 361, where, in a sequential order along the axis 362, a first row may have three cells 404, a second row may have three cells 404, a third row may have three cells 404, a fourth row may have five cells 404, and a fifth row may have three cells 404.

In a fifth exemplary embodiment, and as shown by schematic diagram 440, the collimator 472*e* may be assembled from four collimator segments 442*a* and two collimator segments 442*b* according to a fifth exemplary collimator assembly configuration. Specifically, the four collimator segments 442*a* may each have 16 cells 404 arranged in an array of 4×4 cells 404, and the two collimator segments 442*b* may each have 20 cells 404 arranged in an array of 5×4 cells 404.

In a sixth exemplary embodiment, and as shown by schematic diagram 450, the collimator 472*f* may be assembled from two collimator segments 452*a*, two collimator segments 452*b*, and two collimator segments 452*c* according to a sixth exemplary collimator assembly configuration. Specifically, the two collimator segments 452*a* may each have 17 cells 404 arranged in five rows parallel to the axis 361, where, in a sequential order along the axis 362, a first row may have four cells 404, a second row may have five cells 404, a third row may have four cells 404, a fourth row may have two cells 404, and a fifth row may have two cells 404. Further, the two collimator segments 452*b* may each have 18 cells 404 arranged in five rows parallel to the axis 361, where, in a sequential order along the axis 362, a first row may have five cells 404, a second row may have three cells 404, a third row may have five cells 404, a fourth row may have four cells 404, and a fifth row may have one cell 404. Further, the two collimator segments 452*c* may each have 17 cells 404 arranged in five rows parallel to the axis 361, where, in a sequential order along the axis 362, a first row may have four cells 404, a second row may have five cells 404, a third row may have four cells 404, a fourth row may have two cells 404, and a fifth row may have two cells 404.

In a seventh exemplary embodiment, and as shown by schematic diagram 460, the collimator 472*g* may be assembled from four collimator segments 462*a*, four collimator segments 462*b*, and two collimator segments 462*c* according to a seventh exemplary collimator assembly configuration. Specifically, the four collimator segments 462*a* may each have 10 cells 404 arranged in four rows parallel to the axis 361, where, in a sequential order along the axis 362, a first row may have three cells 404, a second row may have three cells 404, a third row may have two cells 404, and a fourth row may have two cells 404. Further, the four collimator segments 462*b* may each have 9 cells 404 arranged in four rows parallel to the axis 361, where, in a sequential order along the axis 362, a first row may have two cells 404, a second row may have two cells 404, a third row may have three cells 404, and a fourth row may have two cells 404. Further, the two collimator segments 462*c* may each have 14 cells 404 arranged in five rows parallel to the axis 361, where, in a sequential order along the axis 362, a first row may have three cells 404, a second row may have three cells 404, a third row may have three cells 404, a fourth row may have three cells 404, and a fifth row may have two cells 404.

Each collimator segment may include a plurality of cells 404 in various geometric configurations selected to increase a structural integrity of the assembled collimator. The structural integrity of the collimator may depend upon balancing numerous factors, such as an average size of the collimator segments (e.g., an average area of the collimator segments in a plane defining a top view, such as the top views depicted in schematic diagrams 400, 410, 420, 430, 440, 450, and 460 of FIGS. 4A and 4B and the top views depicted in schematic diagrams 330 and 350 of FIG. 3), a total number of the collimator segments, a total number of interfaces 474 between pairs of adjacent collimator segments, an average perimeter of the collimator segments, etc.

In some embodiments, a manufacturing speed to assemble the collimator from the collimator segments may be increased by reducing the average size of the collimator segments, such that multiple collimator segments may be manufactured simultaneously with smaller manufacturing equipment. In additional or alternative embodiments, a perimeter of a given collimator segment may be increased such that additional interfacial surface area (e.g., additional area of surfaces forming the interfaces 474) may be provided for joining the given collimator segment to other collimator segments. Thus, decreasing the average size while increasing the perimeter of the given collimator segment may increase the structural integrity in the finally-assembled collimator.

For example, relatively few collimator segments may result in fewer interfaces 474, which may thereby decrease an overall structural integrity of the assembled collimator. Correspondingly, an increased number of interfaces 474 may increase the overall structural integrity by providing an increased number of locations at which adhesive may be applied to join pairs of adjacent collimator segments as well as increased interfacial tension to restrict movement of collimator segments relative to one another, thereby decreasing inter-segment deviation during manufacturing. However, relatively many collimator segments may decrease the average size thereof, which may thereby reduce a structural strength of any given collimator segment. As such, a balanced selection of the total number of collimator segments in combination with the total number of interfaces 474 provided by the selected collimator assembly configuration may provide greater overall structural integrity to the assembled collimator.

As specific examples of the 10×13 cell configurations, schematic diagram 400 depicts the first exemplary collimator assembly configuration including 6 collimator segments, each of which may be registered to an average of about 22 CZT modules. In contrast, each of the second, third, and fourth exemplary collimator assembly configurations (depicted by schematic diagrams 410, 420, and 430, respectively) include 10 collimator segments, each of which may be registered to an average of about 13 CZT modules.

Further, the first exemplary collimator assembly configuration includes 7 pairwise interfaces 474, as compared to 13, 29, and 45 pairwise interfaces 474 included in the second, third, and fourth exemplary collimator assembly configurations, respectively. As such, the average perimeter of the collimator segments may increase from the first exemplary collimator assembly configuration to the fourth exemplary collimator assembly configuration.

As specific examples of the 8×13 cell configurations, schematic diagrams 440 and 450 respectively depict the fifth and sixth exemplary collimator assembly configurations which each include 6 collimator segments, where each of the 6 collimator segments may be registered to an average of about 17 CZT modules. In contrast, the seventh exemplary collimator assembly configuration (depicted by schematic diagram 460) includes 10 collimator segments, each of which may be registered to an average of about 10 CZT modules. Further, the fifth exemplary collimator assembly configuration includes 7 pairwise interfaces 474, as compared to 33 pairwise interfaces 474 included in each of the sixth and seventh exemplary collimator assembly configurations. As such, the average perimeter of the collimator segments may increase from the fifth exemplary collimator assembly configuration to the seventh exemplary collimator assembly configuration.

The average size of the collimator segments may further be limited by a manufacturing area 406 of the additive manufacturing equipment used to manufacture the collimator segments. As such, in embodiments wherein the collimator is a wide field of view collimator, the manufacturing area 406 may be insufficient to manufacture the collimator in a single piece.

Accordingly, embodiments of systems and methods are provided herein for assembling collimators from multiple collimator segments, which may be joined together at pairwise interfaces. In some embodiments, and as described below in detail with reference to FIGS. 5-6B, pairs of adjacent collimator segments may be further configured so as to removably interlock with one another. Further, manufacturing of configurations of individual collimator segments may be realized with additive manufacturing techniques through facile manipulation of bore width (as described in detail below with reference to FIG. 7), bore shape (as described in detail below with reference to FIG. 8), and variable septal thickness parallel to bore shafts (as described in detail below with reference to FIG. 9).

In the examples shown in FIGS. 4A and 4B, the manufacturing area 406 may be large enough (for example, 8×8 in) to manufacture a collimator segment registered with up to 5×5 CZT modules (e.g., a collimator segment having an array of 5×5 cells 404, such as the collimator segment 402b). As such, the collimator assembly configuration may be selected based upon such a size constraint of the manufacturing area 406. For example, a collimator (e.g., 472a, 472b, 472c, 472d) including 10×13 cells 404 may be assembled from a minimum of 6 collimator segments including a maximum of 5×5 cells 404.

As multiple collimator segments may be registered with any given array of multiple CZT modules (e.g., a 5×5 array), two or more collimator segments may be manufactured within the manufacturing area 406 of the additive manufacturing equipment. Accordingly, schematic diagrams 410, 420, 430, and 460 provide exemplary collimator assembly configurations which each show two collimator segments within the corresponding manufacturing area 406. Further, if the additive manufacturing equipment is supplied with multiple laser units, the two (or more) collimator segments may be manufactured simultaneously. In this way, a total manufacturing time may be reduced by manufacturing multiple collimator segments in parallel.

A relative manufacturing time T for each of the exemplary collimator assembly configurations provided in schematic diagrams 400, 410, 420, 430, 440, 450, and 460 may be determined. A duration T0 may be defined to as a manufacturing time for one cell 404. As specific examples of 10×13 cell configurations, in the first exemplary collimator assembly configuration of schematic diagram 400, since only one collimator segment (e.g., 402a or 402b) may be manufactured within the depicted manufacturing area 406, the relative manufacturing time T may be calculated as [4×(5×4)+2×(5×5)]×T0=130×T0 (e.g., 100% of a maximum possible manufacturing time of 130 cells 404). However, in the second exemplary collimator assembly configuration of schematic diagram 410, two collimator segments (e.g., 412a and 412b) may be manufactured within the depicted manufacturing area 406, and the relative manufacturing time T may be calculated as [6×(5×3)]×T0=90×T0 (e.g., about 69% of a maximum possible manufacturing time of 130 cells 404). It will be appreciated that, in the second exemplary collimator assembly configuration, the collimator segments 412b registering with 5×2 CZT modules may be manufactured simultaneously with the collimator segments 412a registered with 5×3 CZT modules and are therefore not included in determining the relative manufacturing time T. Similarly, two collimator segments may be manufactured within the depicted manufacturing area 406 of the third and fourth exemplary collimator assembly configurations of schematic diagrams 420 and 430 (e.g., the collimator segments 422a and 422b in the schematic diagram 420 and the collimator segments 432a and 432b in the schematic diagram 430). As such, the relative manufacturing time T may be calculated as [4×12+2×17]=82×T0 (e.g., about 63% of a maximum possible manufacturing time of 130 cells 404) for each of the third and fourth exemplary collimator assembly configurations.

As specific examples of 8×13 cell configurations, in the fifth exemplary collimator assembly configuration of schematic diagram 440, since only one collimator segment (e.g., 442a or 442b) may be manufactured within the depicted manufacturing area 406, the relative manufacturing time T may be calculated as [4×(4×4)+2×(5×4)]×T0=104×T0 (e.g., 100% of a maximum possible manufacturing time of 130 cells 404). Similarly, only one collimator segment (e.g., 452a, 45b, or 452c) may be manufactured within the depicted manufacturing area 406 of the sixth exemplary collimator assembly configuration of schematic diagram 450. As such, the relative manufacturing time T may be calculated as [4×17+2×18]=104×T0 for the sixth exemplary collimator assembly configuration. However, in the seventh exemplary collimator assembly configuration of schematic diagram 460, two collimator segments (e.g., 462a and 462b) may be manufactured within the depicted manufacturing area 406, and the relative manufacturing time T may be calculated as [4×10+2×14]×T0=68×T0. It will be appreciated that, in the seventh exemplary collimator assembly configuration, the collimator segments 462b registering with 9 CZT modules may be manufactured simultaneously with the collimator segments 462a registered with 10 CZT modules and are therefore not included in determining the relative manufacturing time T.

Referring now to FIG. 5, schematic diagrams 500, 550, and 560 illustrating a second exemplary assembly process of a collimator 552 from multiple collimator segments 502, 504, 506 are depicted according to one embodiment. In one embodiment, the assembled collimator 552 may be the collimator 122 as implemented in the NM imaging system 100, as shown in FIG. 1. It will be appreciated that schematic diagrams 500 and 550 may depict projected views similar to the projected view of schematic diagram 310, as shown in FIG. 3, and that schematic diagram 560 may depict a top view similar to the top views of schematic diagrams 330 and 350, as shown in FIG. 3.

Schematic diagram 500 depicts six total collimator segments: two collimator segments 502, two collimator segments 504, and two collimator segments 506. It will be appreciated that the two collimator segments 502 may have the same configuration as one another but are rotated around the axes 361 and 362 relative to one another, the two collimator segments 504 may have the same configuration as one another but are rotated around the axis 361 relative to one another, and the two collimator segments 506 may have the same configuration as one another but are rotated around the axes 361 and 362 relative to one another. However, each of the collimator segments 502 may have a different configuration than each of the collimator segments 504 and 506. Similarly, each of the collimator segments 504 may have a different configuration than each of the collimator segments 506.

As represented by bidirectional arrows 508, each of the collimator segments 502, 504, 506 may be configured to join with two or more further collimator segments having complementary interfacial surfaces. As shown in schematic diagram 500, a given collimator segment 502, 504, 506 may have one or more projections 502a, 504a, 506a which may be received by one or more complementary recesses 502b, 504b, 506b on one or more other collimator segments 502, 504, 506 such that a given pair of collimator segments may removably interlock with one another via mating of a given projection to a given recess. As shown in schematic diagram 500, each of the one or more projections 502a, 504a, 506a may include a lengthwise portion (e.g., along the axis 563) of one or more septa included in a given collimator segment 502, 504, 506. As such, complementary lengthwise portions of the one or more septa in the projections 502a, 504a, 506a of a pair of adjacent collimator segments may be aligned to form the entirety of the one or more septa. In this way, the interlocking projections may form at least some of the septa of the finally-formed collimator 552, reducing a space between bores of the pair of adjacent collimator segments as compared to other interlocking configurations (e.g., not including septa on interlocking projections).

Pairs of adjacent collimator segments may be interlocked via two or more projections concurrently mating with two or more complementary recesses, where surfaces of the two or more projections may be in respective face-sharing contact with surfaces of the two or more complementary recesses. As an example, and as shown in schematic diagram 500, one projection 502a of a given collimator segment 502 may mate with one recess 504b of a corresponding collimator segment 504 such that a surface of the projection 502a may be brought into face-sharing contact with a surface of the recess 504b. Concurrently, one recess 502b of the given collimator segment 502 adjacent to the projection 502a may mate with one projection 504a of the corresponding collimator segment 504 adjacent to the recess 504b such that a surface of the projection 504a may be brought into face-sharing contact with a surface of the recess 502b. As another example, and as shown in schematic diagram 500, one projection 502a of a given collimator segment 502 may mate with one recess 506b of a corresponding collimator segment 506 such that a surface of the projection 502a may be brought into face-sharing contact with a surface of the recess 506b. Concurrently, one recess 502b of the given collimator segment 502 adjacent to the projection 502a may mate with one projection 506a of the corresponding collimator segment 506 adjacent to the recess 506b such that a surface of the projection 506a may be brought into face-sharing contact with a surface of the recess 502b. As yet another example, and as shown in schematic diagram 500, one projection 504a of a given collimator segment 504 may mate with one recess 506b of a corresponding collimator segment 506 such that a surface of the projection 504a may be brought into face-sharing contact with a surface of the recess 506b. Concurrently, one recess 504b of the given collimator segment 504 adjacent to the projection 504a may mate with one projection 506a of the corresponding collimator segment 506 adjacent to the recess 506b such that a surface of the projection 506a may be brought into face-sharing contact with a surface of the recess 504b.

In this way, two separate interfaces 554a and 554b may be formed between each pair of adjacent collimator segments. Specifically, and as represented by directional arrow 510, pairs of adjacent collimator segments may be brought into face-sharing contact with one another according to a given collimator assembly configuration such that respective pairs of interfaces 554a and 554b may be formed therebetween.

Each of the interfaces 554a, 554b may then be adhered via application of an adhesive (e.g., a glue, cement, mucilage, paste, etc.). Additional structural support may be provided by the tension between each pair of adjacent collimator segments along the axis 363 (that is, where septa of each of the collimator segments press against one another), restricting movement of the pairs of adjacent collimator segments relative to one another and thereby decreasing inter-segment deviation during manufacturing. Such additional structural support, along with the increased number of interfaces relative to collimator segments not having projections and recesses (e.g., such as the collimator segments 302 of FIG. 3), may help maintain structural integrity even if some of the adhesive loses cohesiveness over time. Once each collimator segment 502, 504, 506 is joined together according to the given collimator assembly configuration, the collimator 552 may be assembled.

The top view depicted in the schematic diagram 560 further illustrates the interfaces 554a, 554b formed between complementary projections and recesses of pairs of adjacent collimator segments in the assembled collimator 552. As shown, solid lines depict interfaces 554a visible in the top view of the schematic diagram 560 and dashed lines depict interfaces 554b obscured in the top view of the schematic diagram 560.

Figure 6A:
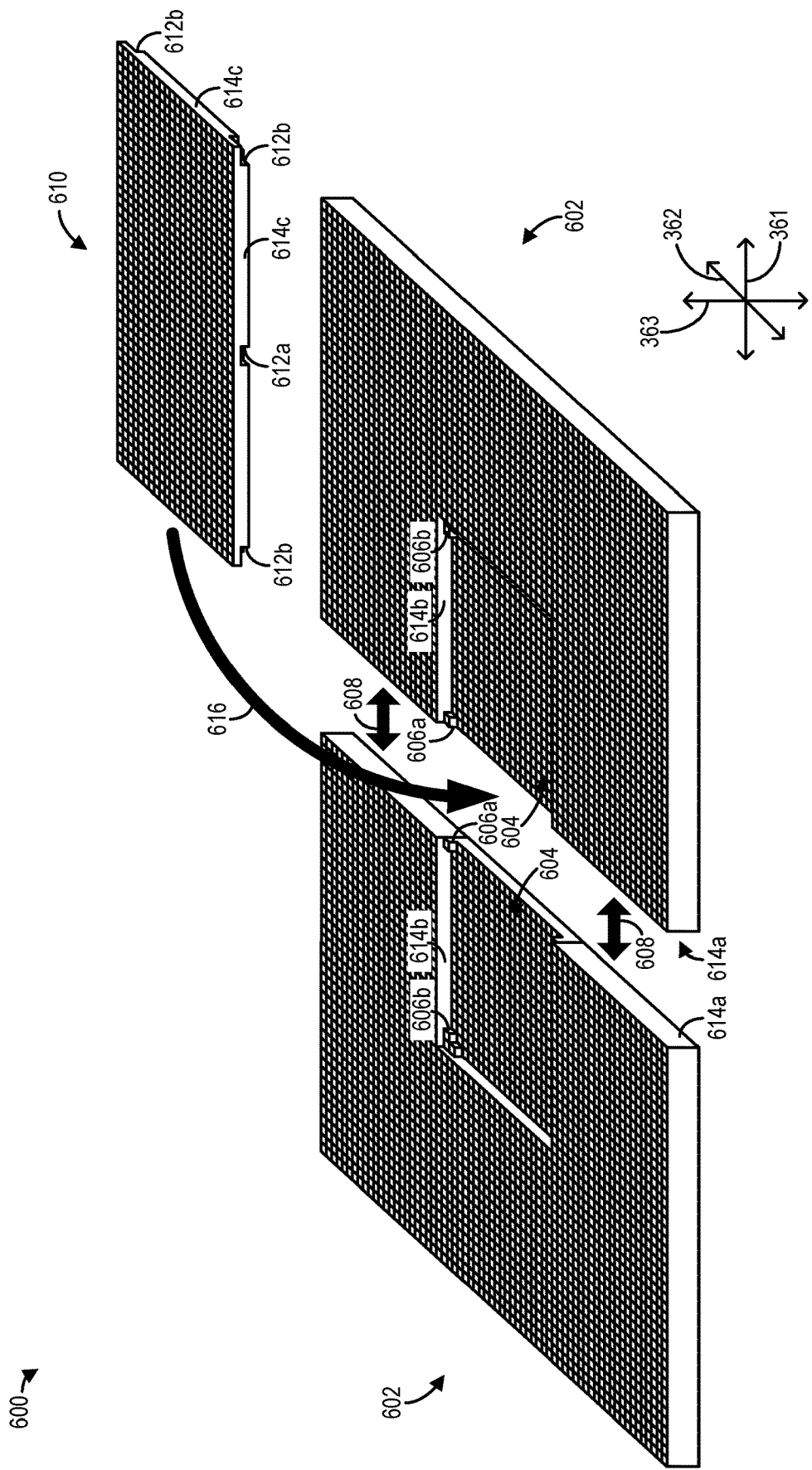
FIGS. 6A and 6B show schematic diagrams illustrating a third exemplary assembly process of the collimator from multiple collimator segments, according to an embodiment.
Figure 6B:
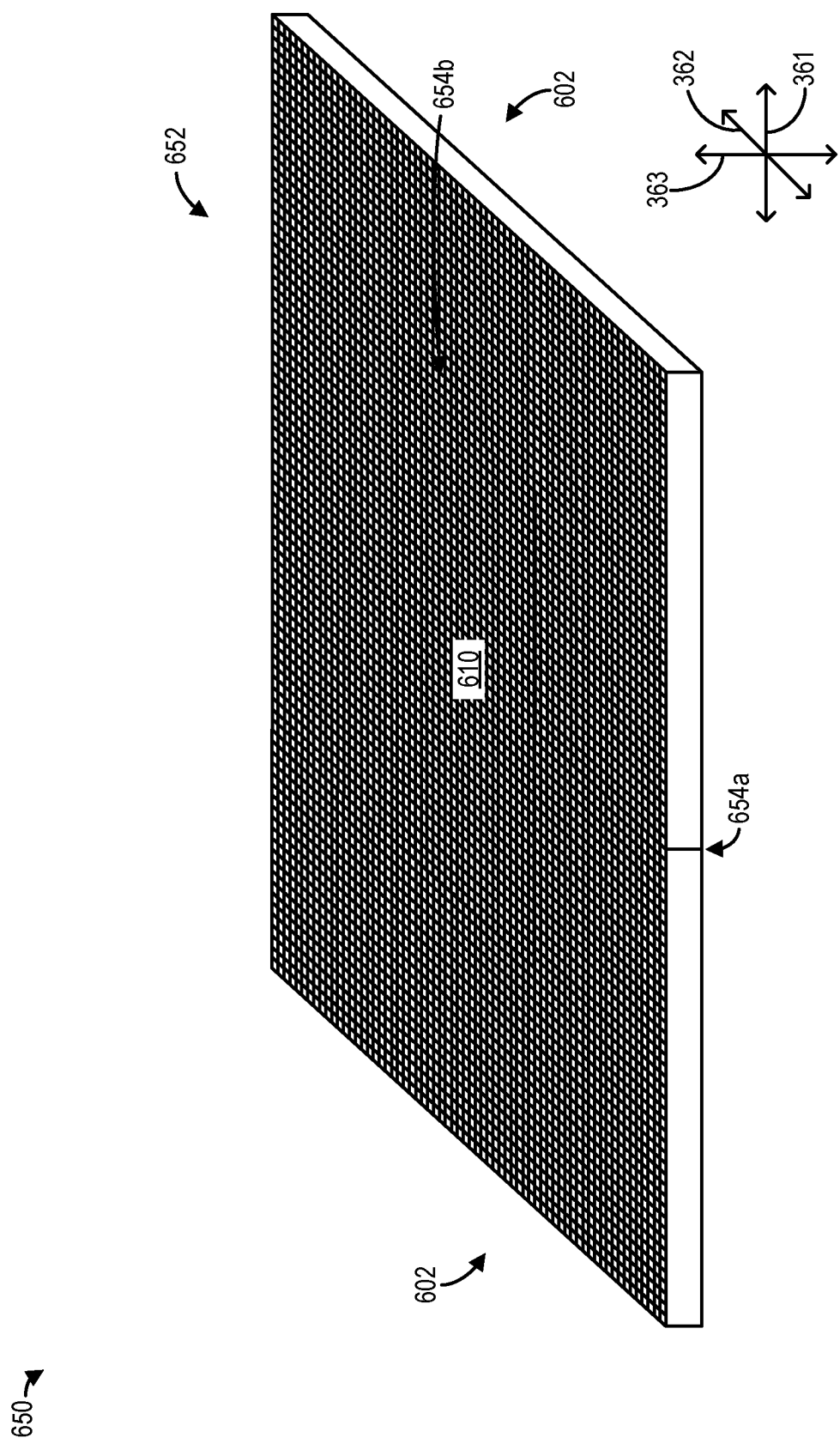

Referring now to FIGS. 6A and 6B, schematic diagrams 600 and 650 illustrating a third exemplary assembly process of a collimator 652 from multiple collimator segments 602, 610 are depicted according to one embodiment. In one embodiment, the assembled collimator 652 may be the collimator 122 as implemented in the NM imaging system 100, as shown in FIG. 1. It will be appreciated that schematic diagrams 600 and 650 may depict projected views similar to the projected view of schematic diagram 310, as shown in FIG. 3.

Schematic diagram 600 depicts two receiving collimator segments 602 and one locking collimator segment 610. It will be appreciated that the two receiving collimator segments 602 may have the same configuration as one another but are rotated around the axes 363 relative to one another.

However, each of the receiving collimator segments 602 may have a different configuration than the locking collimator segment 610.

Each of the two receiving collimator segments 602 may be provided with a recess 604 and one or more projections 606a, 606b. It will be appreciated that, in other embodiments not depicted at FIGS. 6A and 6B, no projections 606a, 606b may be included in the two receiving collimator segments 602. The two receiving collimator segments 602 may be configured such that, when the two receiving collimator segments 602 are joined together (as represented by bidirectional arrows 608), the recesses 604 thereof may receive the locking collimator segment 610.

In examples wherein the one or more projections 606a, 606b are included in the two receiving collimator segments 602, the one or more projections 606a, 606b may interlock with one or more complementary recesses 612a, 612b included in the locking collimator segment 610. As shown in schematic diagram 600, each of the one or more projections 606a, 606b may include a lengthwise portion (e.g., along the axis 363) of one or more septa included in a given receiving collimator segment 602. As such, lengthwise portions of the one or more septa in the projections 606a, 606b of the two receiving collimator segments 602 may be aligned with complementary lengthwise portions of one or septa in the locking collimator segment 610 to form the entirety of the one or more septa. In this way, the interlocking projections may form at least some of the septa of the finally-formed collimator 652, reducing a space between bores of adjacent collimator segments as compared to other interlocking configurations (e.g., not including septa on interlocking projections).

In some embodiments, such as the exemplary embodiment illustrated in schematic diagram 600, each recess 612b included in the locking collimator segment 610 may receive one projection 606b included in one of the receiving collimator segments 602 and each recess 612a included in the locking collimator segment 610 may receive one projection 606a included in each of the receiving collimator segments 602 (that is, each recess 612a may receive two projections 606a). Once the locking collimator segment 610 is interlocked with the two receiving collimator segments 602, the projections 606a may be fit into the recesses 612a such that, when force is applied to pull the two receiving collimator segments 602 apart along the axis 361, the locking collimator segment 610 may provide resistance (via the recesses 612a) to counter the force and decrease the likelihood of the two receiving collimator segments 602 being separated.

In this way, two receiving collimator segments 602 may removably interlock with one locking collimator segment 610. As such, and as shown in schematic diagram 650, interfaces 654b may be formed between each of the receiving collimator segments 602 and the locking collimator segment 610 and an interface 654a may be formed between the two receiving collimator segments 602 themselves.

It will be appreciated that the embodiment depicted in FIGS. 6A and 6B is exemplary, and in some embodiments, the collimator 652 may be formed from a plurality of pairs of receiving collimator segments 602 and a plurality of locking collimator segments 610, each pair of receiving collimator segments 602 interlocking with one of the locking collimator segments 610. For example, multiple collimator assembly configurations corresponding to the collimator assembly configuration depicted in schematic diagram 650 may be arranged in an array and joined together to form the collimator 652. In such embodiments, each pair of receiving collimator segments 602 may include one or more projections 606a, 606b and each locking collimator segment 610 may include one or more complementary recesses 612a, 612b, such that each pair of receiving collimator segments 602 may be interlocked with a corresponding one of the plurality of locking collimator segments 610 via respective mating of the one or more projections 606a, 606b with the one or more complementary recesses 612a, 612b.

Specifically, and as represented by the bidirectional arrows 608, interfacial septa 614a of the two receiving collimator segments 602 may be brought into face-sharing contact with one another according to a given collimator assembly configuration such that one interface 654a may be formed therebetween. Accordingly, the recesses 604 of the receiving collimator segments 602 may be aligned with one another along the axis 361, such that pairs of the projections 606a may be brought into face-sharing contact with one another. Then, as represented by directional arrow 616, the locking collimator segment 610 may be removably interlocked with each of the two receiving collimator segments 602. As such, interfacial septa 614c of the locking collimator segment 610 may be brought into face-sharing contact with interfacial septa 614b of the two receiving collimator segments 602 according to the given collimator assembly configuration such that four interfaces 654b may be formed therebetween (e.g., for each pair of interfacial septa 614b and 614c normal to a plane defined by the axes 361 and 362).

In some embodiments, the locking collimator segment 610 in the assembled collimator 652 may be configured to be removable, such that the locking collimator segment 610 may be exchanged for another locking collimator segment 610, e.g., to suit a different imaging application. Further, it will be appreciated that the locking collimator segment 610 may be increased in total area relative to the two receiving collimator segments 602. For example, the locking collimator segment 610 may be increased in total area in a plane defined by the axes 361 and 362, such that the total area of the locking collimator segment 610 may be substantially equal to a combined area of the two receiving collimator segments 602 and the two receiving collimator segments 602 may be overlapped by an orthographic projection of the locking collimator segment 610 along the axis 363. Accordingly, lengthwise portions of the septa in the locking collimator segment 610 may be aligned with complementary lengthwise portions of the septa in the two receiving collimator segments 602 to form the entirety of the septa. Optionally, in such embodiments, the two receiving collimator segments 602 may be configured as a single receiving collimator segment (e.g., having no interface 654a). In this way, the collimator 652 may be assembled in a layered configuration, wherein a portion of the collimator 652 (e.g., the locking collimator segment 610) may be exchanged.

In some embodiments, each of the interfaces 654a, 654b may be adhered via application of an adhesive (e.g., a glue, cement, mucilage, paste, etc.). Additional structural support may be provided by the tension between the receiving collimator segments 602 and the locking collimator segment 610 along the axis 361 (that is, where the projections 606a, 606b removably interlock with the recesses 612a, 612b) and along the axis 363 (that is, where septa of each of the receiving collimator segments 602 press against septa of the locking collimator segment 610), restricting movement of the collimator segments relative to one another and thereby decreasing inter-segment deviation during manufacturing. Such additional structural support, along with the increased number of interfaces relative to collimator segments not having projections and recesses (e.g., such as the collimator segments 302 of FIG. 3), may help maintain structural integrity even if some of the adhesive loses cohesiveness over time. Once each receiving collimator segment 602 and locking collimator segment 610 is joined together according to the given collimator assembly configuration, the collimator 652 may be assembled.

Figure 7:
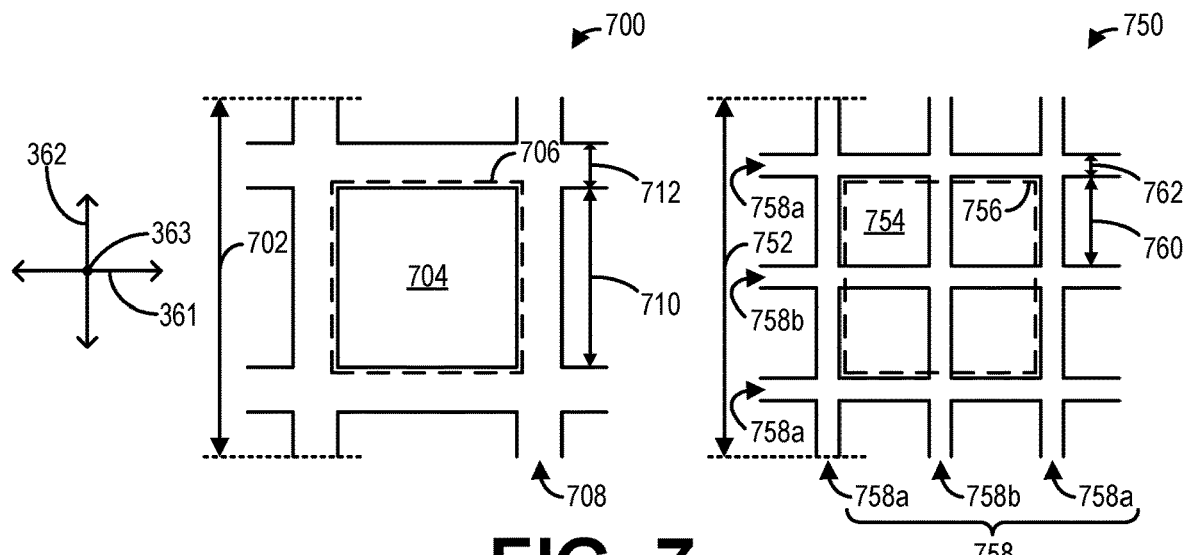
FIG. 7 shows schematic diagrams illustrating geometric considerations of exemplary bore widths for two exemplary collimator segments, according to an embodiment.

Referring now to FIG. 7, schematic diagrams 700 and 750 illustrating geometric considerations of exemplary bore widths for two exemplary collimator segments are depicted according to one embodiment. It will be appreciated that schematic diagrams 700 and 750 may depict top views of portions of the two exemplary collimator segments similar to the top views of schematic diagrams 330 and 350, as shown in FIG. 3. In one embodiment, the collimator segments may be assembled to form a collimator, such as the collimator 352 of FIG. 3 or the collimator 122 of FIG. 1. In additional or alternative embodiments, the bores of the collimator may be uniquely registered to pixels of a CZT module in a detector unit (e.g., 114), and the septa of the collimator may align with edges of the pixels.

An exemplary portion of a first collimator segment is depicted in schematic diagram 700, including an exemplary bore 704 circumscribed by exemplary septa 708. Further, a pixel 706 is depicted as a dashed box to illustrate that the pixel 706 (and thereby the CZT module including a plurality of pixels 706) may be positioned underneath the bores 704 and the septa 708 of the first collimator segment along the axis 363. Specifically, the exemplary portion of the first collimator segment may be a square top view defined by a length 702 in the plane defined by the axes 361 and 362. In the schematic diagram 700, the bore 704 may be configured as a square defined by a bore width 710. The bore width 710 may be substantially similar to a width of the pixel 706 to which the bore 704 may be registered (e.g., 2.5 mm), such that a projection of the bore 704 along the axis 363 onto the pixel 706 may circumscribe the pixel or may substantially align with sides of the pixel 706. The septa 708 may be defined by a septal thickness 712. Further, the septa 708 may project along the axis 363 onto spaces between the pixels 706 of the CZT module.

An exemplary portion of a second collimator segment is depicted in schematic diagram 750, including four exemplary bores 754 circumscribed by exemplary septa 758. Further, a pixel 756 is depicted as a dashed box to illustrate that the pixel 756 (and thereby the CZT module including a plurality of pixels 756) may be positioned underneath the bores 754 and the septa 758 of the second collimator segment along the axis 363.

Specifically, the exemplary portion of the second collimator segment may be a square top view defined by the length 702 in the plane defined by the axes 361 and 362. It will be appreciated that the length 702 depicted in the schematic diagram 750 may be substantially equivalent to the length 752 depicted in the schematic diagram 700. In the schematic diagram 750, the bore 754 may be configured as a square defined by a bore width 760. The bore width 760 may be about half of the bore width 710, such that a total area of the four bores 754 may be about the same as a total area of the one bore 704. As such, the four bores 754 may be uniquely registered to one pixel 756 of the CZT module. Said another way, the bores 754 may include groups of bores (e.g., four bores), where each group of bores may be uniquely registered to one pixel 756 of the CZT module. It will be appreciated that the dimensions of the pixel 706 depicted in the schematic diagram 700 may be substantially equivalent to the dimensions of the pixel 756 depicted in the schematic diagram 750. The septa 758 may be defined by a septal thickness 762. In the top view depicted by schematic diagram 750, the septa 758 may include four septa 758a and two septa 758b, where the four septa 758a may circumscribe the four bores 754 and may project along the axis 363 onto spaces between the pixels 756 of the CZT module, and the two septa 758b may be interposed between the four bores 754 and may project along the axis 363 onto the pixels 756 themselves. However, since the septal thickness 762 may be about half of the septal thickness 712, a majority of an area of the pixels 756 may be open to the bores 754 such that most incoming radiation may still pass through the bores 754 to be acquired by the pixels 756. In this way, the septa 758 may be configured to be thinner than the gaps between the pixels 756 of the CZT module and a total number of bores 754 may be increased (e.g., quadrupled), which may improve a sensitivity of an overall detector unit without sacrificing substantial imaging resolution.

Referring now to FIG. 8, schematic diagrams 800, 810, 820, 830, and 840 respectively illustrating exemplary collimator segment configurations of collimator segments 802, 812, 822, 832, and 842 are depicted. It will be appreciated that schematic diagrams 800, 810, 820, 830, and 840 may depict top views of exemplary collimator segments configurations similar to the top views of schematic diagrams 330 and 350, as shown in FIG. 3. In one embodiment, the collimator segments may be assembled to form a collimator, such as the collimator 352 of FIG. 3 or the collimator 122 of FIG. 1. In additional or alternative embodiments, the bores of the collimator may be registered to pixels of a CZT module in a detector unit (e.g., 114), and the septa of the collimator may align with edges of the pixels.

As shown in schematic diagrams 800, 810, 820, 830, and 840, the bores and septa of the exemplary collimator segment configurations may conform to a variety of shapes and relative sizes. For instance, the bores may be configured to have a number of bore shapes. As a first example, schematic diagram 800 illustrates a collimator segment 802 having a first exemplary collimator segment configuration. Specifically, the first exemplary collimator segment configuration may include bores 804 circumscribed by septa 808, wherein each of the bores 804 may project a bore shape of a hexagon in a plane defined by the axes 361 and 362. As a second example, schematic diagram 810 illustrates a collimator segment 812 having a second exemplary collimator segment configuration. Specifically, the second exemplary collimator segment configuration may include bores 814 circumscribed by septa 818, wherein each of the bores 814 may project a bore shape of a circle in a plane defined by the axes 361 and 362. As a third example, schematic diagram 820 illustrates a collimator segment 822 having a third exemplary collimator segment configuration. Specifically, the third exemplary collimator configuration may include bores 824 circumscribed by septa 828, wherein each of the bores 824 may project a bore shape of a square in a plane defined by the axes 361 and 362. It will therefore be appreciated that though the bores are depicted as squares in FIGS. 3 and 5-7 for purposes of illustration, the bores may be configured as any shape or combination of shapes contemplatable by those of at least ordinary skill in the art (including the bore shapes depicted in FIG. 8, as well as other bore shapes not explicitly shown herein, e.g., triangles, trapezoids, rectangles, etc.).

Further, the septa may be configured to have variable septal thickness. As an example, schematic diagram 830 depicts a collimator segment 832 having a fourth exemplary collimator segment configuration. Specifically, the fourth exemplary collimator segment configuration may include bores 834 circumscribed by septa 838, wherein the septa 838 may include central septal 837 and interfacial septa 839, and wherein the interfacial septa 839 may have a larger septal thickness (e.g., substantially twice as thick) than the central septa 837. Collimator segments 832 having the fourth exemplary collimator segment configuration may be assembled into a collimator having an increased overall structural integrity, as interfaces between pairs of adjacent collimator segments 832 may be reinforced by the increased septal thickness of the interfacial septa 839.

Said another way, in schematic diagram 830, the central septa 837 may have a smaller septal thickness (e.g., substantially half as thick) than the interfacial septa 839. In embodiments where septal penetration is an issue of lower concern (e.g., when the collimator is decreased in overall length, such as when the collimator is a dual-pitch collimator), thinner central septa 837 may be employed to increase imaging sensitivity and decrease manufacturing costs.

As another example, schematic diagram 840 depicts a collimator segment 842 having a fifth exemplary collimator segment configuration. Specifically, the fifth exemplary collimator segment configuration may include bores 844 circumscribed by septa 848, wherein the bores 844 may include central bores 843 and peripheral bores 845, and wherein the septa 848 around the peripheral bores 845 may have a larger septal thickness than other septa 848. Said another way, the peripheral bores 845 may have a smaller bore width than the central bores 843. In some embodiments, the bore width may decrease the closer a given bore 844 is to a center of the collimator segment 842. Collimator segments 842 having the fifth exemplary collimator segment configuration may be assembled into a collimator having an increased overall structural integrity, as interfaces between pairs of adjacent collimator segments 842 may be reinforced by the increased septal thickness of the septa 848 around the peripheral bores 845.

Referring now to FIG. 9, schematic diagram 900 illustrating geometric considerations of radiation penetrating septa 908 of a portion of a collimator is depicted. It will be appreciated that schematic diagram 900 depicts a cross-sectional view of the collimator in a plane defined by the axes 361 and 363, where the axis 362 is normal to the plane of the cross-sectional view. In one embodiment, the collimator may be the collimator 352 of FIG. 3 or the collimator 122 of FIG. 1.

As shown in schematic diagram 900, a septal thickness may be variable along a length of septa 908 (e.g., along the axis 363). For example, the septa 908 depicted in schematic diagram 900 may be characterized by an exterior septal thickness 902 and an interior septal thickness 906, where the interior septal thickness 906 is the septal thickness at a midpoint along a length of the septa 908 and the exterior septal thickness 906 is the septal thickness at endpoints of the length of the septa 908. As shown, the interior septal thickness 906 may be larger than (e.g., about twice as thick as) the exterior septal thickness 902. As further shown, the interior septal thickness 906 which may linearly taper to the exterior septal thickness 902 along the length of the septa 908. However, it will be appreciated by those of at least ordinary skill in the art that nonlinear tapering of the septal thickness may be contemplated within the scope of the present disclosure.

If more radiation (e.g., photons) is collected by pixels of a CZT module in a detector unit (e.g., 114), an imaging sensitivity of the detector unit may be increased. However, radiation may pass through a collimator (e.g., 122) registered to the detector unit at various angles, which may affect an imaging resolution of the detector unit. Specifically, radiation travelling along paths of radiation substantially parallel to the axis 363 may be acquired by an array of pixels in a plane defined by the axes 361 and 362 with higher imaging resolution than radiation travelling along paths of radiation substantially not parallel to the axis 363. This is because radiation travelling along paths of radiation substantially not parallel to the axis 363 may penetrate the septa 908 and thereby be attenuated.

For example, a first path of radiation 910 is shown in schematic diagram 900 as passing through the collimator parallel to the length of bores 904 (e.g., parallel to the axis 363). As shown, the first path of radiation 910 may not penetrate the septa 908 prior to passing through a given bore 904. As such, when the collimator (e.g., 122) is registered to the CZT module of the detector unit (e.g., 114), radiation travelling along the first path of radiation 910 may pass through the given bore 904 and be acquired by pixels with high fidelity. As another example, a second path of radiation 912 is shown in schematic diagram as passing through the collimator at a nonzero angle relative to the length of the bores 904 (e.g., in a plane defined by the axes 361 and 363). As shown, the second path of radiation 912 may not penetrate the septa 908 prior to passing through a given bore 904. As such, and similar to the first path of radiation 910, when the collimator is registered to the CZT module of the detector unit, radiation travelling along the second path of radiation 912 may pass through the given bore 904 and be acquired by pixels with high fidelity.

However, a third path of radiation 914 may be angled so as to penetrate a given septum 908 at about a midpoint thereof. Since the septal thickness is equal to or near the larger interior septal thickness 906 at the midpoint of the given septum 908, less radiation travelling along the third path of radiation 914 may penetrate the given septum 908. Said another way, fewer photons may fully penetrate through the septa 908 along non-parallel paths of radiation. As such, by providing a larger septal thickness near a midpoint of the septa 908 of the collimator, imaging resolution may be increased without sacrificing substantial imaging sensitivity. That is, more imaging sensitivity may be sacrificed if the septal thickness of the entire septum 908 were thicker, as less radiation travelling substantially parallel to the axis 363 would be acquired (for example, radiation travelling along the second path of radiation 912 would penetrate one or more septa 908 if each septum 908 had a constant septal thickness equivalent to the interior septal thickness 906).

In some embodiments, a wide field of view collimator may be assembled from collimator segments manufactured via additive manufacturing techniques. Because additive manufacturing techniques may form structures by stacking printed or sintered layers of material along a given dimension, variations in patterns of the stacked layers along the given dimension may be easily achieved. For example, a collimator segment including the septa 908 having the configuration depicted in schematic diagram 900 may be formed by stacking printed or sintered layers along the axis 363. In this way, additive manufacturing techniques may form collimator segments for wide field of view collimators as single components (e.g., having no adhesive within the collimator segments themselves). In contrast, conventional manufacturing techniques may first form two separate halves of the collimator segment (bisected along the axis 363) and then adhere the two halves together with an adhesive to form the collimator segment.

Figure 10:
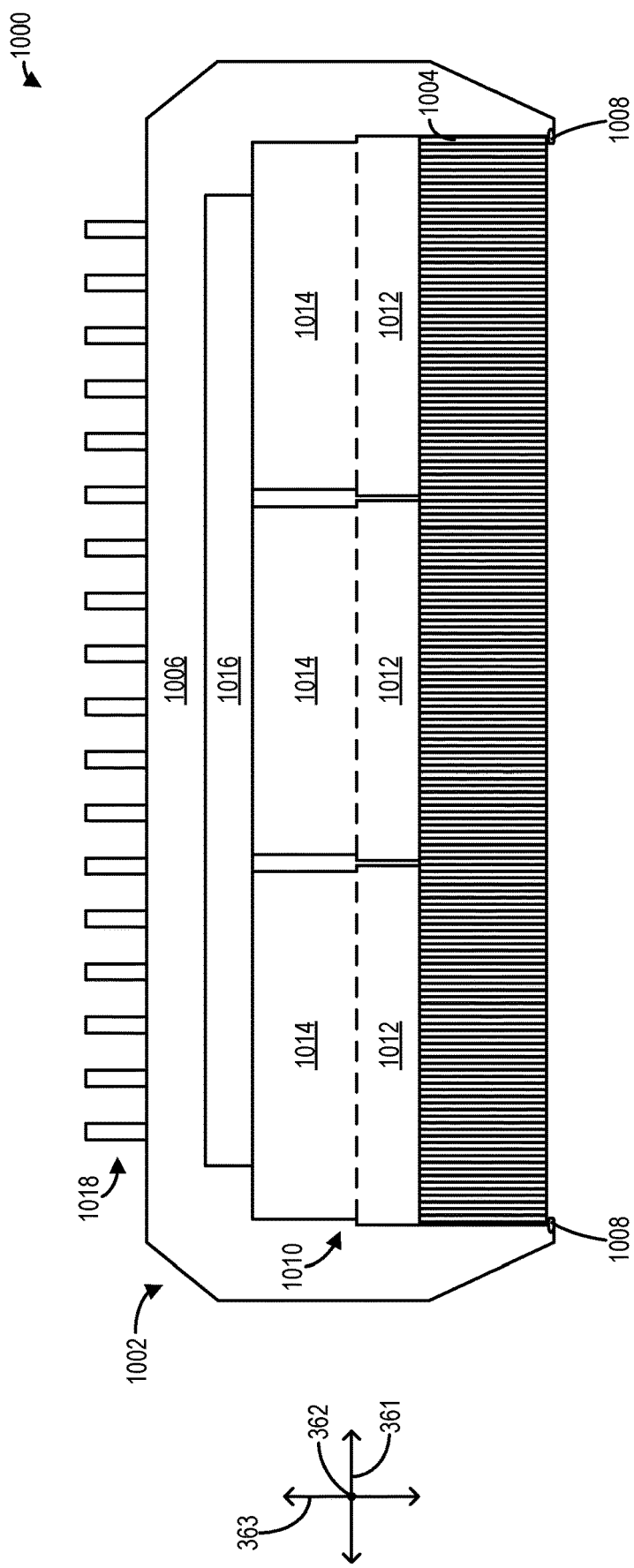
FIG. 10 shows a schematic diagram illustrating a detector unit for use in the NM imaging system.

Referring now to FIG. 10, schematic diagram 1000 illustrating an exemplary detector unit 1002 including a collimator 1004 is depicted. It will be appreciated that schematic diagram 1000 depicts a cross-sectional view of the detector unit 1002 similar to the cross-sectional view of schematic diagram 900, as shown in FIG. 9. In one embodiment, the detector unit 1002 may be the detector unit 114 of FIG. 1. As such, the collimator 1004 may be the collimator 122 of FIG. 1. In another embodiment, the collimator 1004 may be the collimator 352 of FIG. 3. As such, the collimator 1008 may be a wide field of view collimator assembled from a plurality of additively-manufactured collimator segments.

The detector unit 1002 may include a casing 1006 which may house one or more of the various components of the detector unit 1002, where the casing 1006 may be a frame or other support structure. The casing 1006 may be made of a high-density material, such as lead or tungsten, for example. The collimator 1004 may be disposed within the casing 1006. In specific embodiments wherein the collimator 1004 is exchangeable, the collimator 1004 may be removably fixed in place by a pair of adjustable locking mechanisms 1008 such that the collimator 1004 may be attached and detached upon application of pressure to each of the pair of adjustable locking mechanisms 1008.

Three CZT modules 1010 are further shown in the depicted embodiment, each indicative of a row of multiple CZT modules 1010. For example, each of the three rows of CZT modules 1010 may be respectively aligned with the depicted CZT modules 1010 and may extend along the axis 362, such that one or more CZT modules 1010 may be in front of the plane of the cross-sectional view and one and/or one or more CZT modules 1010 may be behind the plane of the cross-sectional view.

The collimator 1004 may include a plurality of bores and a plurality of septa, which may be configured to receive and narrow incoming radiation (e.g., gamma rays) for the CZT modules 1010. Specifically, a plurality of bores may be registered to a plurality of pixels of CZT detector plates 1012 respectively situated in the CZT modules 1010, and the plurality of septa may align with edges of the plurality of pixels. Accordingly, the incoming radiation may be passed to the plurality of pixels. Each of the CZT modules 1010 may further include electronics 1014 (e.g., output electronics to output detected events) conductively coupling a respective CZT detector plate 1012 to a printed circuit board (PCB) 1016, such that NM imaging data may be acquired based on the incoming radiation. The NM imaging data may then be passed to the controller unit (e.g., 130) and the processing unit (e.g., 150) of the NM imaging system (e.g., 100), as described above with reference to FIG. 1. A heat sink (e.g., air or water cooling) 1018 with a fan (not shown) may be disposed on, or positioned within, the casing 1006, so as to prevent overheating of the various components therein during operation of the detector unit 1002.

In this way, collimators assembled from additively manufactured collimator segments are provided for wide field of view nuclear medicine imaging. A given collimator segment may be interlocked with an adjacent collimator segment via mating of a projection with a recess. The projection may include a lengthwise portion of at least one septum of the collimator segment such that, when mated with the recess, lengthwise portions of the at least one septum in the projection of the given collimator segment and on the adjacent collimator segment may be aligned to form the entirety of the at least one septum. A technical effect of interlocking pairs of adjacent collimator segments according to such collimator segment configurations is that a space between bores on the pairs of adjacent collimator segments may be reduced as interlocking projections may form at least some of the septa of the finally-formed collimator (e.g., as compared to other collimator segment configurations not including septa on interlocking projections). Additionally, a septal thickness may be varied within a given collimator segment and/or within a given septum. As a first example, septal thickness of interfacial septa (e.g., adjacent to inter-segment interfaces) may be decreased relative to central septa in the given collimator segment. As a second example, septal thickness in an interior of each septum may be increased relative to an exterior thereof. A technical effect of varying the septal thickness is that septal penetration may be decreased (e.g., due to increased septal thickness in the interior of each septum) while further increasing the structural integrity (e.g., due to increased septal thickness of interfacial septa).

In one embodiment, a collimator comprises a plurality of collimator segments comprising a plurality of septa, wherein at least one collimator segment is interlocked with at least one adjacent collimator segment via mating of one or more projections with one or more complementary recesses, each of the one or more projections comprising a lengthwise portion of at least one septum of the plurality of septa. In a first example of the collimator, the at least one collimator segment being interlocked with the at least one adjacent collimator segment comprises a plurality of interfacial septa of the at least one collimator segment being in respective face-sharing contact with a plurality of interfacial septa of the at least one adjacent collimator segment to form a plurality of interfaces. In a second example of the collimator, optionally including the first example of the collimator, an adhesive is included between surfaces of interfacial septa forming the plurality of interfaces, the adhesive being restricted in the collimator to the surfaces of the interfacial septa forming the plurality of interfaces. In a third example of the collimator, optionally including one or more of the first and second examples of the collimator, each collimator segment comprises a plurality of interfacial septa having a first septal thickness and a plurality of central septa having a second septal thickness, the first septal thickness being larger than the second septal thickness. In a fourth example of the collimator, optionally including one or more of the first through third examples of the collimator, each collimator segment comprises a plurality of central bores having a first bore width and a plurality of peripheral bores having a second bore width, the first bore width being larger than the second bore width. In a fifth example of the collimator, optionally including one or more of the first through fourth examples of the collimator, the at least one collimator segment being interlocked with the at least one adjacent collimator segment via mating of the one or more projections with the one or more complementary recesses comprises each collimator segment of the plurality of collimator segments being interlocked with one or more other collimator segments of the plurality of collimator segments via mating of the one or more projections with the one or more complementary recesses. In a sixth example of the collimator, optionally including one or more of the first through fifth examples of the collimator, the at least collimator segment is interlocked with the at least one adjacent collimator segment via mating of two or more projections with two or more complementary recesses, surfaces of the two or more projections being in respective face-sharing contact with surfaces of the two or more complementary recesses. In a seventh example of the collimator, optionally including one or more of the first through sixth examples of the collimator, the plurality of collimator segments comprises one or more pairs of receiving collimator segments and one or more locking collimator segments, each pair of receiving collimator segments interlocked with one of the one or more locking collimator segments. In an eighth example of the collimator, optionally including one or more of the first through seventh examples of the collimator, each pair of receiving collimator segments comprises the one or more projections and each locking collimator segment comprises the one or more complementary recesses, and each pair of receiving collimator segments is interlocked with the one of the one or more locking collimator segments via mating of the one or more projections with the one or more complementary recesses. In a ninth example of the collimator, optionally including one or more of the first through eighth examples of the collimator, each septum of the plurality of septa has an interior septal thickness and an exterior septal thickness, the interior septal thickness being larger than the exterior septal thickness. In a tenth example of the collimator, optionally including one or more of the first through ninth examples of the collimator, each collimator segment is manufactured as a single piece without adhesive.

In another embodiment, a medical imaging system comprises a plurality of detector units, each of the plurality of detector units comprising a plurality of cadmium zinc telluride (CZT) modules and a tungsten collimator comprising a plurality of bores interposed between a plurality of septa, the tungsten collimator comprising a plurality of interlocked tungsten collimator segments, wherein the plurality of interlocked tungsten collimator segments are joined via projecting septa mated to complementary recesses, and wherein each of the CZT modules is uniquely registered to one of the plurality of interlocked tungsten collimator segments. In a first example of the medical imaging system, the CZT modules comprise a plurality of pixels, each of the plurality of bores being uniquely registered to one of the plurality of pixels. In a second example of the medical imaging system, optionally including the first example of the medical imaging system, the plurality of bores comprises groups of bores, each group of bores being uniquely registered to one of the plurality of pixels. In a third example of the medical imaging system, optionally including one or more of the first and second examples of the medical imaging system, a pitch of the tungsten collimator is twice a pitch of a corresponding one of the plurality of detector units.

In yet another embodiment, a method comprises forming a plurality of collimator segments, each collimator segment being formed by repeatedly dispersing and sintering a metal powder, and interlocking one or more pairs of the plurality of collimator segments by overlapping lengthwise portions of septa in each pair of collimator segments, wherein each collimator segment comprises tungsten and an additional metal. In a first example of the method, the additional metal is one or more of lead, thallium, molybdenum, tantalum, bismuth, copper, iron, and antimony. In a second example of the method, optionally including the first example of the method, the metal powder comprises a first powder composed of tungsten and a second metal powder composed of the additional metal. In a third example of the method, optionally including one or more of the first and second examples of the method, the metal powder comprises a tungsten powder coated in the additional metal. In a fourth example of the method, optionally including one or more of the first through third examples of the method, the metal powder comprises a tungsten powder, and forming the plurality of collimator segments comprises forming a plurality of tungsten structures, each tungsten structure being formed by repeatedly dispersing and sintering the tungsten powder, heating the additional metal to a molten state, and dipping the plurality of tungsten structures in the additional metal.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
    a plurality of detector units, each of the plurality of detector units comprising a plurality of cadmium zinc telluride (CZT) modules and a tungsten collimator comprising a plurality of bores interposed between a plurality of septa, the tungsten collimator comprising:
    a plurality of tungsten collimator segments, wherein the plurality of tungsten collimator segments are joined to at least one segment to form a combined collimator, and wherein each of the CZT modules comprise a plurality of pixels, each of the plurality of bores being uniquely registered to one of the plurality of pixels.

2. The medical imaging system of claim 1, wherein the plurality of bores comprises groups of bores, each group of bores being uniquely registered to one of the plurality of pixels.

3. The medical imaging system of claim 1, wherein a pitch of the tungsten collimator is twice a pitch of a corresponding one of the plurality of detector units.

4. The medical imaging system of claim 1, wherein the plurality of collimator segments comprising a plurality of septa, wherein at least one collimator segment is interlocked with at least one adjacent collimator segment via mating of one or more projections with one or more complementary recesses, each of the one or more projections comprising a lengthwise portion of at least one septum of the plurality of septa.

5. The medical imaging system of claim 1, wherein the at least one collimator segment being interlocked with the at least one adjacent collimator segment comprises:
    a plurality of interfacial septa of the at least one collimator segment being in respective face-sharing contact with a plurality of interfacial septa of the at least one adjacent collimator segment to form a plurality of interfaces.

6. The medical imaging system of claim 5, wherein an adhesive is included between surfaces of interfacial septa forming the plurality of interfaces, the adhesive being restricted in the collimator to the surfaces of the interfacial septa forming the plurality of interfaces.

7. The medical imaging system of claim 1, wherein each collimator segment comprises a plurality of interfacial septa having a first septal thickness and a plurality of central septa having a second septal thickness, the first septal thickness being larger than the second septal thickness.

8. The medical imaging system of claim 1, wherein each collimator segment comprises a plurality of central bores having a first bore width and a plurality of peripheral bores having a second bore width, the first bore width being larger than the second bore width.

9. The medical imaging system of claim 1, wherein the at least one collimator segment being interlocked with the at least one adjacent collimator segment via mating of the one or more projections with the one or more complementary recesses comprises:
    each collimator segment of the plurality of collimator segments being interlocked with one or more other collimator segments of the plurality of collimator segments via mating of the one or more projections with the one or more complementary recesses.

10. The medical imaging system of claim 1, wherein the at least one collimator segment is interlocked with the at least one adjacent collimator segment via mating of two or more projections with two or more complementary recesses, surfaces of the two or more projections being in respective face-sharing contact with surfaces of the two or more complementary recesses.

11. The medical imaging system of claim 1, wherein the plurality of collimator segments comprises one or more pairs of receiving collimator segments and one or more locking collimator segments, each pair of receiving collimator segments interlocked with one of the one or more locking collimator segments.

12. The medical imaging system of claim 11, wherein each pair of receiving collimator segments comprises the one or more projections and each locking collimator segment comprises the one or more complementary recesses, and wherein each pair of receiving collimator segments is interlocked with the one of the one or more locking collimator segments via mating of the one or more projections with the one or more complementary recesses.

13. The medical imaging system of claim 1, wherein each septum of the plurality of septa has an interior septal thickness and an exterior septal thickness, the interior septal thickness being larger than the exterior septal thickness.

14. The medical imaging system of claim 13, wherein each collimator segment is manufactured as a single piece without adhesive.

15. The medical imaging system of claim 1, wherein each of the CZT modules is uniquely registered to one of the plurality of collimator segments.

16. The medical imaging system of claim 1, wherein each collimator segment is formed by repeatedly dispersing and sintering a metal powder; and
    wherein each collimator segment comprises tungsten and an additional metal.

17. The medical imaging system of claim 16, wherein the additional metal is one or more of lead, thallium, molybdenum, tantalum, bismuth, copper, iron, and antimony.

18. The medical imaging system of claim 16, wherein the metal powder comprises a first powder composed of tungsten and a second metal powder composed of the additional metal.

19. The medical imaging system of claim 16, wherein the metal powder comprises a tungsten powder coated in the additional metal.

20. The medical imaging system of claim 16, wherein the metal powder comprises a tungsten powder, and
    wherein forming the plurality of collimator segments comprises:
        forming a plurality of tungsten structures, each tungsten structure being formed by repeatedly dispersing and sintering the tungsten powder;
        heating the additional metal to a molten state; and
        dipping the plurality of tungsten structures in the additional metal.

* * * * *